(12) United States Patent
Zou et al.

(10) Patent No.: US 6,825,039 B2
(45) Date of Patent: Nov. 30, 2004

(54) PLANT PYRUVATE DEHYDROGENASE KINASE GENE

(75) Inventors: Jitao Zou, Saskatoon (CA); David C. Taylor, Saskatoon (CA)

(73) Assignee: National Research Council of Canada, Ottawa (CA)

( * ) Notice: Subject to any disclaimer, the term of this patent is extended or adjusted under 35 U.S.C. 154(b) by 118 days.

(21) Appl. No.: 10/202,428

(22) Filed: Jul. 23, 2002

(65) Prior Publication Data

US 2003/0084472 A1 May 1, 2003

Related U.S. Application Data

(63) Continuation of application No. 09/355,912, filed on Oct. 15, 1999, now Pat. No. 6,500,670.
(60) Provisional application No. 60/038,815, filed on Feb. 10, 1997.

(51) Int. Cl.[7] .................... C12N 15/86; C12N 15/00; C12N 5/04; C12N 15/09; C12N 15/63
(52) U.S. Cl. .................... 435/466; 435/440; 435/419; 435/320.1; 435/252.3; 800/281
(58) Field of Search ................... 435/466, 440, 435/419, 320.1, 252.3; 536/23.1; 800/281

(56) References Cited

U.S. PATENT DOCUMENTS 6,265,636 B1   7/2001   Randall et al.

FOREIGN PATENT DOCUMENTS

WO    WO 99/67403    12/1999

OTHER PUBLICATIONS

Kirill M. Popov et al., "Primary Structure of Pyruvate Dehydrogenase Kinase Establishes a New Family of Eukaryotic Protein Kinases," The Journal of Biological Chemistry, vol. 268, No. 35, Issue of Dec. 15, pp. 26602–26606, 1993.
Ramavedi Gudi et al., "Diversity of the Pyruvate Dehydrogenase Kinase Gene Family in Humans," The Journal of Biological Chemistry, vol. 270, No. 48, Issue of Dec. 1, pp. 28989–28994, 1995.
E. Ellen Reid et al., "Pyruvate Dehydrogenase Complex from Higher Plant Mitochondria and Proplastids," Plant Physiol. (1977) vol. 59, pp. 842–848.
Christopher P.L. Grof. et al., "Mitochondrial Pyruvate Dehydrogenase," Plant Physiol. (1995) vol. 108, pp. 1623–1629.
Tom Newman et al., Genes Galore: A Summary of Methods for Accessing Results from Large–Scale Partial Sequencing of Anonymous Arabidopsis cDNA Clones, Plant Physiol. (1994) vol. 106, pp. 1241–1255.
Gibco BRL 1991 Nucleic Acids New Products p. 746.
Zou, Jitao et al., "Effects of antisense repression of an Arabidopsis thaliana pyruvate dehydrogenase kinase cDNA on plant development," National Research Council of Canada, Plant Biotechnology Institute, 110 Gymnasium Place, Saskatoon, Saskatchewan, Canada, S7N 0W9, Plant Molecular Biology 41:837–849, 1999, © 1999 Kluwer Academic Plublishers, Printed in the Netherlands.
Thelen, Jay J. et al., "Pyruvate dehydrogenase kinase from Arabidopsis thaliana: a protein histidine kinase that phosphorylates serine residues," Biochem. J. (2000) 349, 195–201, (Printed in Great Britain).
Mooney, Brian P. et al., Biochemistry Department, University of Missouri, Columbia Missouri 65211; and Plant Genetics Research Unit, USDA, ARS, Columbia, Missouri, 65211, "Histidine Modifying Agents Abolish Pyruvate Dehydrogenase Kinase Activity," Biochemical and Biophysical Research Communications, 267, 500–503 (2000).
Thelen, Jay J. et al., "Molecular Analysis of Two Pyruvate Dehydrogenase Kinases from Maize," The Journal of Biological Chemistry, vol. 273, No. 41, Issue of Oct. 9, 1998, pp. 26618–26623.
Printout of GenBank Accession No.: AF038585.
Printout of GenBank Accession No.: AF038586.
PCT International Search Report, PCT/CA98/00096, dated Jul. 23, 1998.

Primary Examiner—James Ketter
Assistant Examiner—Konstantina Katcheves
(74) Attorney, Agent, or Firm—TraskBritt

(57) ABSTRACT

The present invention relates to the isolation, purification, characterization and use of a mitochondrial pyruvate dehydrogenase kinase (PDHK) gene (SEQ ID NO:1) (pYA5; ATCC No 209562) from the Brassicaceae (specifically Arabidopsis thaliana). The invention includes isolated and purified DNA of the stated sequence and relates to methods of regulating fatty acid synthesis, seed oil content, seed size/weight, flowering time, vegetative growth, respiration rate and generation time using the gene and to tissues and plants transformed with the gene. The invention also relates to transgenic plants, plant tissues and plant seeds having a genome containing an introduced DNA sequence of SEQ ID NO:1, or a part of SEQ ID NO:1 characterized in that said sequence has been introduced in an anti-sense or sense orientation, and a method of producing such plants and plant seeds. The invention also relates to substantially homologous DNA sequences from plants encoding proteins with deduced amino acid sequences of 25% or greater identity, and 50% or greater similarity, isolated and/or characterized by known methods using the sequence information of SEQ ID NO:1, and to parts of reduced length that are still able to function as inhibitors of gene expression by use in an anti-sense, co-suppression or other gene silencing technologies.

6 Claims, 14 Drawing Sheets

FIG. 2A

```
  1: t cca tct gcg cac ttc ttt cgt cca gtc gat gat aat aac ggt gg
 46: a gaa cga cgg agg cgg gcg acg tta ggg ttt cta atc att tct ct
 91: c tct tag acg ctt atg gca gtg aag aaa gcc tgc gaa atg ttc cc
                        M   A   V   K   K   A   C   E   M   F   P 136: g aag agt ttg atc gaa gat gtt cac aaa tgg ggt tgc atg aag ca
       K   S   L   I   E   D   V   H   K   W   G   C   M   K   Q 181: a acc ggt gtt agc ctt aga tac atg atg gag ttt ggt tcc aaa cc
       T   G   V   S   L   R   Y   M   M   E   F   G   S   K   P 226: t act gag agg aat ctt ttg att tct gct cag ttt ttg cat aag ga
       T   E   R   N   L   L   I   S   A   Q   F   L   H   K   E 271: g ctt ccg att cgc gtc gcc agg aga gcg atc gaa ctc cag acg ct
       L   P   I   R   V   A   R   R   A   I   E   L   Q   T   L 316: t cct tat ggt ctc tct gat aaa cct gcc gtt ttg aag gtg cgg ga
       P   Y   G   L   S   D   K   P   A   V   L   K   V   R   D 361: t tgg tat ttg gaa tct ttc agg gac atg aga gca ttt cct gag at
       W   Y   L   E   S   F   R   D   M   R   A   F   P   E   I 406: t aag gat tcg ggt gac gag aaa gat ttc act cag atg att aag gc
       K   D   S   G   D   E   K   D   F   T   Q   M   I   K   A 451: t gtc aaa gta agg cat aac aat gtg gtt ccc atg atg gct ttg gg
       V   K   V   R   H   N   N   V   V   P   M   M   A   L   G 496: t gtt aat cag ctc aag aaa gga atg aat tct gga aat ctt gat ga
       V   N   Q   L   K   K   G   M   N   S   G   N   L   D   E 541: g att cat cag ttt ctt gat cgt ttc tac ttg tcg cga atc ggg at
       I   H   Q   F   L   D   R   F   Y   L   S   R   I   G   I 586: c cgg atg ctt att ggg cag cac gtt gag ttg cat aat cca aat cc
       R   M   L   I   G   Q   H   V   E   L   H   N   P   N   P
```

FIG. 2B

```
 631: a ccg ctt cat aca gtg ggt tat ata cac aca aag atg tct cct at
         P   L   H   T   V   G   Y   I   H   T   K   M   S   P   M 676: g gag gta gca agg aat gca agt gaa gat gct cgg tca att tgt tt
         E   V   A   R   N   A   S   E   D   A   R   S   I   C   F 721: c cga gag tac ggt tct gca ccg gaa ata aac ata tat ggc gat cc
         R   E   Y   G   S   A   P   E   I   N   I   Y   G   D   P 766: c agt ttc acc ttt ccg tat gtt cca acg cat ttg gat ctt atg at
         S   F   T   F   P   Y   V   P   T   H   L   D   L   M   M 811: g tat gag cta gtc aag aac tct cta cgt gct gtc caa gag cga tt
         Y   E   L   V   K   N   S   L   R   A   V   Q   E   R   F 856: t gtt gac tct gat aga gtt gca cca cca atc cgc att ata gtt gc
         V   D   S   D   R   V   A   P   P   I   R   I   I   V   A 901: t gat gga atc gaa gat gtt act ata aag gtc tca gat gaa ggt gg
         D   G   I   E   D   V   T   I   K   V   S   D   E   G   G 946: a ggt ata gca aga agc ggt ctt ccc aga ata ttc acc tat ctt ta
         G   I   A   R   S   G   L   P   R   I   F   T   Y   L   Y 991: c agc act gca aga aac ccg ctt gag gag gat gtc gat tta gga at
         S   T   A   R   N   P   L   E   E   D   V   D   L   G   I 1036: a gct gat gtt ccc ggg act atg ggt gga tat ggt tat ggt ctt cc
         A   D   V   P   G   T   M   G   G   Y   G   Y   G   L   P 1081: a att agt cgc ttg tat gct cga tat ttc ggt gga gat ttg cag at
         I   S   R   L   Y   A   R   Y   F   G   G   D   L   Q   I 1126: c ata tcc atg gaa gga tat ggg act gat gca tac ttg cac ttg tc
         I   S   M   E   G   Y   G   T   D   A   Y   L   H   L   S 1171: t cgc ctt gga gat tcg caa gag cct tta ccc tga gaa cat ctc ta
         R   L   G   D   S   Q   E   P   L   P   *

1216: t gtc agg caa agt aaa gaa agc ttt gac atg tat tta tgg tag at
1261: g agg gat atc tac aat act caa tta ttt atg ctt ttc cag ttt ct
1306: g cta atg tac aga cta cag aca tta ttt tct cgt att acg ctt tc
1351: t tga ttt tag act cag ata tgg agc ttt ttc caa gtg agt taa tc
1396: t cct atg att tgt ttt ggt tcg atc caa aac cac ctt gta tcc ga
1441: a aaa aaa aaa aaa aaa a
```

FIG. 3

The amino acid sequence alignment of the *Arabidopsis* PDH kinase (Ya5p) with other mammalian mitochondrial ketoacid dehydrogenase kinase. Pdhk I, porcine PDH kinase subunit I. Pdhk II, porcine PDH kinase subunit II. Bckdhk, porcine branched chain alpha-ketoacid dehydrogenase kinase. Dots indicate gaps. Identical amino acid residues are highlighted in bold upper case type.

```
Ya5p     MAVKKA..........................................CEMFPK
pdhkI    MrwfRAllknaslagapkyiehfskfsp.....................spLsmK
pdhkII   MrLaRllrggtsvrplcavpcasrslasdsasgsgpasesgvpgqvdfyarfspspLsmK
bckdhk   MiLtsvlgsgprsgsslwpllgsslslrvrstsatdthhvelare.........rsktvt ya5p     SLIEDVHKWGCMKQTGVSLR..YMMEFGSKPTERNLLISAQFLHKELPIRVARRAIELQT
pdhkI    qfLDfgssnACeKtSftfLRqelpVrlAnimkEiNLLpdrvlstpsVqLvqSwyvqsLld
pdhkII   qfLDfgsvnACeKtsfMfLRqelpVrlAnimkEisLLpdnllrtpsVqLvqSwyiqsLQe
bckdhk   SfyNqsaidvvaekPSVrLtptmMLysGrsqdgshLLksGrYLqqELPVRiAhRikgfvv ya5p     LPYGLSDKPAVLKVRDWYLESFRDMRAFPEIKDSGDEKDFTQMIKAVKVRHNNVVPMMAL
pdhkI    ImefLdkdPedhRtlsqFtDAlvtIRn......................RHNNVVPtMAq
pdhkII   LldfkdksAedaKtiyeFtDTvirIRn......................RHNDVIPtMAq
bckdhk   flsSLvatlPyctVhElYIrAFqkLtdFPpIKDqADEaQYcQLVRqLlddHkDVVtLLAe ya5p     GVNQLKKGMNSGNLDEIH.Q.FLDRFYLSRIGIRMLIGQHVELHNPNPPLHTVGYI...H
pdhkI    GVlEyKdTygddpVsNqmiQyFLDRFYLSRISIRMLInQtLifdgStnPaHPkhgsidpn
pdhkII   GVNEyKeSfgSdpVtsqmvQyFLDRFYMSRISIRMLLnQHslLfgGkGSpshrkhIgsin
bckdhk   GlrEsrKhIEdekL..Vry..FLDKtltSRLGIRMLaThHLaLH..EdkpdfVGiIs...

ya5p     TKMSPMEVARNASEDARSICFREYGSAPEINIYGDPS......FTFPYVPTHLDLMMYEL
pdhkI    PncSvsDVvKDAyDmAklLCdKyYmASPDLEIqevnAtnatqpihmvYVPSHLyhMLFEL
pdhkII   PncdvvEViKDGyENARrLCdlyYvnSPELELeelnAkspgqpiqvvYVPSHLyhMVFEL
bckdhk   TRLSPkkIiekwvDfARrLCeHkYGnAPrVrInGhvAa......rFPFIPmpLDyILpEL ya5p     VKNSLRAVQERFVDSDRVAPPIRIIVADGIEDVTIKVSDEGGGIARSGLP....RIFTYL
pdhkI    fKNAMRAtvEshesSlt.lPPIkIMVAlGeEDLSIKMSDrGGGVPlrkIe....RLFSYM
pdhkII   fKNAMRAtmEhhaDkgv.yPPIqvhVtlGeEDLTVKMSDrGGGVPlrkId....RLFnYM
bckdhk   LKNAMRAtmEshLDtpynvPdVvItIANndvDLiIrISDrGGGIAHkdLdrvmdyhFTta ya5p     YSTARNPLEEDVDLGIADVPGTMG........GYGYGLPISRLYARYFGGDLQIISMEGY
pdhkI    YSTAptPqpgtg.gTp......LA........GFGYGLPISRLYAKYFQGDLQLFSMEGf
pdhkII   YSTAprPrvEtsravp......LA........GFGYGLPISRLYAqYFqGDLkLySLEGY
bckdhk   ....eaStQDprisPLfDhldThSggqsgpmhGFGFGLPtSRaYAeYlGGsLQLqSLQGi ya5p     GTDAYLHLSRLGDSQEPLP
pdhkI    GTDAviyLkaLSTdSverlpvynksawrhyqtiqeagdwcvpstepkntyrvs
pdhkII   GTDAviyikaLSTeSierlpvynkaawkhyrtnheaddwcvpsrepkdmttfrss
bckdhk   GTDv.LHrSRhidgreesfri
```

Northern Blot Analysis of PDK Gene Expression in Arabidopsis thaliana
RNA was extracted from flowers (F), seedlings(L), young siliques(YS) and maturing siliques (MS).

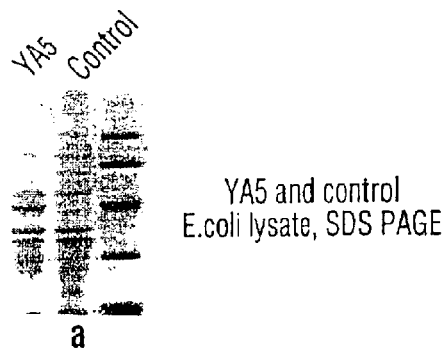
YA5 and control
E.coli lysate, SDS PAGE
FIG. 7A
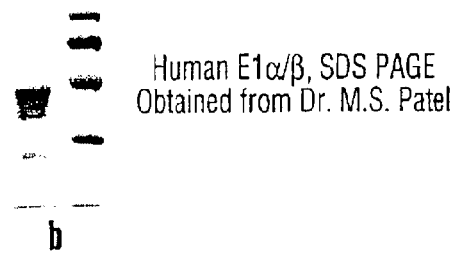
Human E1α/β, SDS PAGE
Obtained from Dr. M.S. Patel
FIG. 7B
Phosphorylation of PDHE1 subunit:
YA5 E.coli lysate, Human E1α/β, γ-$^{32}$P-ATP, Mg$^{++}$, pH 7.0
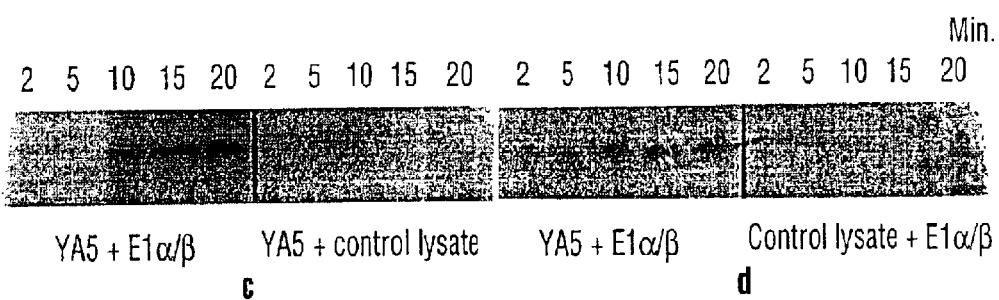
FIG. 7C  FIG. 7D

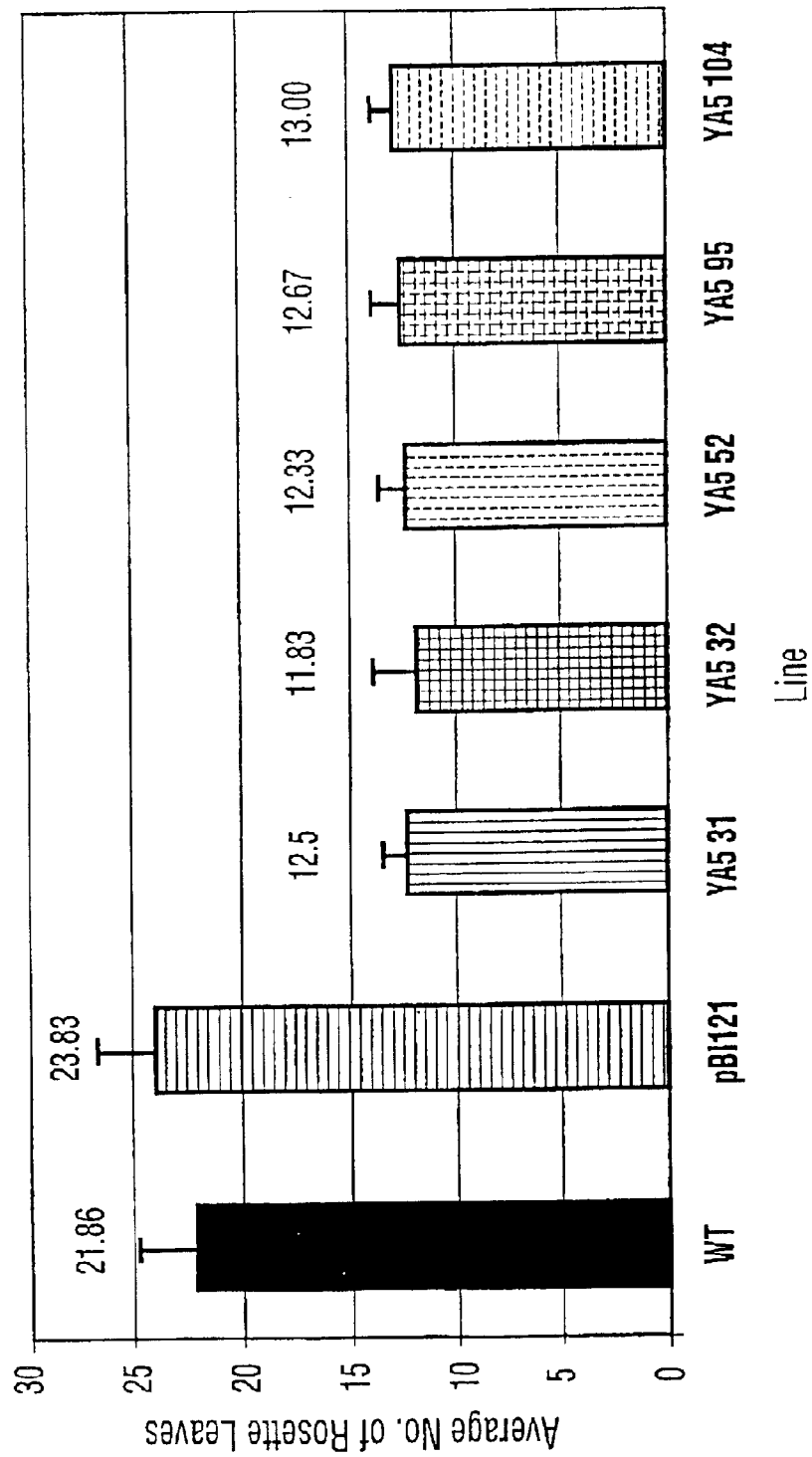

SEQUENCE LISTING

<160> NUMBER OF SEQ ID NOS: 9

<210> SEQ ID NO 1
<211> LENGTH: 1457
<212> TYPE: DNA
<213> ORGANISM: Arabidopsis thaliana

<400> SEQUENCE: 1

| | | | | | |
|---|---|---|---|---|---|
| tccatctgcg | cacttctttc | gtccagtcga | tgataataac | ggtggagaac | gacggaggcg | 60 |
| ggcgacgtta | gggtttctaa | tcatttctct | ctcttagacg | cttatggcag | tgaagaaagc | 120 |
| ctgcgaaatg | ttcccgaaga | gtttgatcga | agatgttcac | aaatggggtt | gcatgaagca | 180 |
| aaccggtgtt | agccttagat | acatgatgga | gtttggttcc | aaacctactg | agaggaatct | 240 |
| tttgatttct | gctcagtttt | tgcataagga | gcttccgatt | cgcgtcgcca | ggagagcgat | 300 |
| cgaactccag | acgcttcctt | atggtctctc | tgataaacct | gccgttttga | aggtgcggga | 360 |
| ttggtatttg | gaatctttca | gggacatgag | agcatttcct | gagattaagg | attcgggtga | 420 |
| cgagaaagat | ttcactcaga | tgattaaggc | tgtcaaagta | aggcataaca | atgtggttcc | 480 |
| catgatggct | ttgggtgtta | atcagctcaa | gaaggaatg | aattctggaa | atcttgatga | 540 |
| gattcatcag | tttcttgatc | gtttctactt | gtcgcgaatc | gggatccgga | tgcttattgg | 600 |
| gcagcacgtt | gagttgcata | atccaaatcc | accgcttcat | acagtgggtt | atatacacac | 660 |
| aaagatgtct | cctatggagg | tagcaaggaa | tgcaagtgaa | gatgctcggt | caatttgttt | 720 |
| ccgagagtac | ggttctgcac | cggaaataaa | catatatggc | gatcccagtt | tcacctttcc | 780 |
| gtatgttcca | acgcatttgg | atcttatgat | gtatgagcta | gtcaagaact | ctctacgtgc | 840 |
| tgtccaagag | cgatttgttg | actctgatag | agttgcacca | ccaatccgca | ttatagttgc | 900 |
| tgatggaatc | gaagatgtta | ctataaaggt | ctcagatgaa | ggtggaggta | tagcaagaag | 960 |
| cggtcttccc | agaatattca | cctatcttta | cagcactgca | agaaacccgc | ttgaggagga | 1020 |
| tgtcgattta | ggaatagctg | atgttcccgg | gactatgggt | ggatatggtt | atggtcttcc | 1080 |
| aattagtcgc | ttgtatgctc | gatatttcgg | tggagatttg | cagatcatat | ccatggaagg | 1140 |
| atatgggact | gatgcatact | tgcacttgtc | tcgccttgga | gattcgcaag | agcctttacc | 1200 |
| ctgagaacat | ctctatgtca | ggcaaagtaa | agaaagcttt | gacatgtatt | tatggtagat | 1260 |
| gagggatatc | tacaatactc | aattatttat | gcttttccag | tttctgctaa | tgtacagact | 1320 |
| acagacatta | ttttctcgta | ttacgctttc | ttgattttag | actcagatat | ggagcttttt | 1380 |
| ccaagtgagt | taatctccta | tgatttgttt | tggttcgatc | caaaaccacc | ttgtatccga | 1440 |
| aaaaaaaaa | aaaaaaa | | | | | 1457 |

<210> SEQ ID NO 2
<211> LENGTH: 366
<212> TYPE: PRT
<213> ORGANISM: Arabidopsis thaliana

<400> SEQUENCE: 2

Met Ala Val Lys Lys Ala Cys Glu Met Phe Pro Lys Ser Leu Ile Glu
1               5                   10                  15

Asp Val His Lys Trp Gly Cys Met Lys Gln Thr Gly Val Ser Leu Arg
            20                  25                  30

Tyr Met Met Glu Phe Gly Ser Lys Pro Thr Glu Arg Asn Leu Leu Ile
        35                  40                  45

```
Ser Ala Gln Phe Leu His Lys Glu Leu Pro Ile Arg Val Ala Arg Arg
     50                  55                  60

Ala Ile Glu Leu Gln Thr Leu Pro Tyr Gly Leu Ser Asp Lys Pro Ala
 65                  70                  75                  80

Val Leu Lys Val Arg Asp Trp Tyr Leu Glu Ser Phe Arg Asp Met Arg
                 85                  90                  95

Ala Phe Pro Glu Ile Lys Asp Ser Gly Asp Glu Lys Asp Phe Thr Gln
            100                 105                 110

Met Ile Lys Ala Val Lys Val Arg His Asn Asn Val Val Pro Met Met
            115                 120                 125

Ala Leu Gly Val Asn Gln Leu Lys Lys Gly Met Asn Ser Gly Asn Leu
            130                 135                 140

Asp Glu Ile His Gln Phe Leu Asp Arg Phe Tyr Leu Ser Arg Ile Gly
145                 150                 155                 160

Ile Arg Met Leu Ile Gly Gln His Val Glu Leu His Asn Pro Asn Pro
                165                 170                 175

Pro Leu His Thr Val Gly Tyr Ile His Thr Lys Met Ser Pro Met Glu
            180                 185                 190

Val Ala Arg Asn Ala Ser Glu Asp Ala Arg Ser Ile Cys Phe Arg Glu
            195                 200                 205

Tyr Gly Ser Ala Pro Glu Ile Asn Ile Tyr Gly Asp Pro Ser Phe Thr
            210                 215                 220

Phe Pro Tyr Val Pro Thr His Leu Asp Leu Met Met Tyr Glu Leu Val
225                 230                 235                 240

Lys Asn Ser Leu Arg Ala Val Gln Glu Arg Phe Val Asp Ser Asp Arg
                245                 250                 255

Val Ala Pro Pro Ile Arg Ile Ile Val Ala Asp Gly Ile Glu Asp Val
            260                 265                 270

Thr Ile Lys Val Ser Asp Glu Gly Gly Gly Ile Ala Arg Ser Gly Leu
            275                 280                 285

Pro Arg Ile Phe Thr Tyr Leu Tyr Ser Thr Ala Arg Asn Pro Leu Glu
            290                 295                 300

Glu Asp Val Asp Leu Gly Ile Ala Asp Val Pro Gly Thr Met Gly Gly
305                 310                 315                 320

Tyr Gly Tyr Gly Leu Pro Ile Ser Arg Leu Tyr Ala Arg Tyr Phe Gly
                325                 330                 335

Gly Asp Leu Gln Ile Ile Ser Met Glu Gly Tyr Gly Thr Asp Ala Tyr
            340                 345                 350

Leu His Leu Ser Arg Leu Gly Asp Ser Gln Glu Pro Leu Pro
            355                 360                 365

<210> SEQ ID NO 3
<211> LENGTH: 405
<212> TYPE: PRT
<213> ORGANISM: Porcine PDH kinase subunit I

<400> SEQUENCE: 3

Met Arg Trp Phe Arg Ala Leu Leu Lys Asn Ala Ser Leu Ala Gly Ala
 1               5                  10                  15

Pro Lys Tyr Ile Glu His Phe Ser Lys Phe Ser Pro Ser Pro Leu Ser
             20                  25                  30

Met Lys Gln Phe Leu Asp Phe Gly Ser Ser Asn Ala Cys Glu Lys Thr
             35                  40                  45

Ser Phe Thr Phe Leu Arg Gln Glu Leu Pro Val Arg Leu Ala Asn Ile
 50                  55                  60
```

```
Met Lys Glu Ile Asn Leu Leu Pro Asp Arg Val Leu Ser Thr Pro Ser
 65                  70                  75                  80

Val Gln Leu Val Gln Ser Trp Tyr Val Gln Ser Leu Leu Asp Ile Met
                 85                  90                  95

Glu Phe Leu Asp Lys Asp Pro Glu Asp His Arg Thr Leu Ser Gln Phe
             100                 105                 110

Thr Asp Ala Leu Val Thr Ile Arg Asn Arg His Asn Asn Val Val Pro
         115                 120                 125

Thr Met Ala Gln Gly Val Leu Glu Tyr Lys Asp Thr Tyr Gly Asp Asp
     130                 135                 140

Pro Val Ser Asn Gln Asn Ile Gln Tyr Phe Leu Asp Arg Phe Tyr Leu
145                 150                 155                 160

Ser Arg Ile Ser Ile Arg Met Leu Ile Asn Gln Thr Leu Ile Phe Asp
                 165                 170                 175

Gly Ser Thr Asn Pro Ala His Pro Lys His Gly Ser Ile Asp Pro Asn
             180                 185                 190

Pro Asn Cys Ser Val Ser Asp Val Val Lys Asp Ala Tyr Asp Met Ala
         195                 200                 205

Lys Leu Leu Cys Asp Lys Tyr Tyr Met Ala Ser Pro Asp Leu Glu Ile
     210                 215                 220

Gln Glu Val Asn Ala Thr Asn Ala Thr Gln Pro Ile His Met Val Tyr
225                 230                 235                 240

Val Pro Ser His Leu Tyr His Met Leu Phe Glu Leu Phe Lys Asn Ala
                 245                 250                 255

Met Arg Ala Thr Val Glu Ser His Glu Ser Ser Leu Thr Leu Pro Pro
             260                 265                 270

Ile Lys Ile Met Val Ala Leu Gly Glu Glu Asp Leu Ser Ile Lys Met
         275                 280                 285

Ser Asp Arg Gly Gly Val Pro Leu Arg Lys Ile Glu Arg Leu Phe
     290                 295                 300

Ser Tyr Met Tyr Ser Thr Ala Pro Thr Pro Gln Pro Gly Thr Gly Gly
305                 310                 315                 320

Thr Pro Leu Ala Gly Phe Gly Tyr Gly Leu Pro Ile Ser Arg Leu Tyr
                 325                 330                 335

Ala Lys Tyr Phe Gln Gly Asp Leu Gln Leu Phe Ser Met Glu Gly Phe
             340                 345                 350

Gly Thr Asp Ala Val Ile Tyr Leu Lys Ala Leu Ser Thr Asp Ser Val
         355                 360                 365

Glu Arg Leu Pro Val Tyr Asn Lys Ser Ala Trp Arg His Tyr Gln Thr
     370                 375                 380

Ile Gln Glu Ala Gly Asp Trp Cys Val Pro Ser Thr Glu Pro Lys Asn
385                 390                 395                 400

Thr Tyr Arg Val Ser
            405

<210> SEQ ID NO 4
<211> LENGTH: 434
<212> TYPE: PRT
<213> ORGANISM: Porcine PDH kinase subunit II

<400> SEQUENCE: 4

Met Arg Leu Ala Arg Leu Leu Arg Gly Gly Thr Ser Val Arg Pro Leu
1               5                  10                  15

Cys Ala Val Pro Cys Ala Ser Arg Ser Leu Ala Ser Asp Ser Ala Ser
```

-continued

```
                20                  25                  30
Gly Ser Gly Pro Ala Ser Glu Ser Gly Val Pro Gly Gln Val Asp Phe
            35                  40                  45
Tyr Ala Arg Phe Ser Pro Ser Pro Leu Ser Met Lys Gln Phe Leu Asp
        50                  55                  60
Phe Gly Ser Val Asn Ala Cys Glu Lys Thr Ser Phe Met Phe Leu Arg
65                  70                  75                  80
Gln Glu Leu Pro Val Arg Leu Ala Asn Ile Met Lys Glu Ile Ser Leu
                85                  90                  95
Leu Pro Asp Asn Leu Leu Arg Thr Pro Ser Val Gln Leu Val Gln Ser
            100                 105                 110
Trp Tyr Ile Gln Ser Leu Gln Glu Leu Leu Asp Phe Lys Asp Lys Ser
        115                 120                 125
Ala Glu Asp Ala Lys Thr Ile Tyr Glu Phe Thr Asp Thr Val Ile Arg
    130                 135                 140
Ile Arg Asn Arg His Asn Asp Val Ile Pro Thr Met Ala Gln Gly Val
145                 150                 155                 160
Asn Glu Tyr Lys Glu Ser Phe Gly Ser Asp Pro Val Thr Ser Gln Asn
                165                 170                 175
Val Gln Tyr Phe Leu Asp Arg Phe Tyr Met Ser Arg Ile Ser Ile Arg
            180                 185                 190
Met Leu Leu Asn Gln His Ser Leu Leu Phe Gly Gly Lys Gly Ser Pro
        195                 200                 205
Ser His Arg Lys His Ile Gly Ser Ile Asn Pro Asn Cys Asp Val Val
    210                 215                 220
Glu Val Ile Lys Asp Gly Tyr Glu Asn Ala Arg Arg Leu Cys Asp Leu
225                 230                 235                 240
Tyr Tyr Val Asn Ser Pro Glu Leu Glu Leu Glu Leu Asn Ala Lys
                245                 250                 255
Ser Pro Gly Gln Pro Ile Gln Val Val Tyr Val Pro Ser His Leu Tyr
            260                 265                 270
His Met Val Phe Glu Leu Phe Lys Asn Ala Met Arg Ala Thr Met Glu
        275                 280                 285
His His Ala Asp Lys Gly Val Tyr Pro Pro Ile Gln Val His Val Thr
    290                 295                 300
Leu Gly Glu Glu Asp Leu Thr Val Lys Met Ser Asp Arg Gly Gly Gly
305                 310                 315                 320
Val Pro Leu Arg Lys Ile Asp Arg Leu Phe Asn Tyr Met Tyr Ser Thr
                325                 330                 335
Ala Pro Arg Pro Arg Val Glu Thr Ser Arg Ala Val Pro Leu Ala Gly
            340                 345                 350
Phe Gly Tyr Gly Leu Pro Ile Ser Arg Leu Tyr Ala Gln Tyr Phe Gln
        355                 360                 365
Gly Asp Leu Lys Leu Tyr Ser Leu Glu Gly Tyr Gly Thr Asp Ala Val
    370                 375                 380
Ile Tyr Ile Lys Ala Leu Ser Thr Glu Ser Ile Glu Arg Leu Pro Val
385                 390                 395                 400
Tyr Asn Lys Ala Ala Trp Lys His Tyr Arg Thr Asn His Glu Ala Asp
                405                 410                 415
Asp Trp Cys Val Pro Ser Arg Glu Pro Lys Asp Met Thr Thr Phe Arg
            420                 425                 430
Ser Ser
```

<210> SEQ ID NO 5
<211> LENGTH: 412
<212> TYPE: PRT
<213> ORGANISM: Porcine branched chain alpha-ketoacid dehydrogenase kinase

<400> SEQUENCE: 5

```
Met Ile Leu Thr Ser Val Leu Gly Ser Gly Pro Arg Gly Ser Ser
1               5                   10                  15

Leu Trp Pro Leu Leu Gly Ser Ser Leu Ser Leu Arg Val Arg Ser Thr
            20                  25                  30

Ser Ala Thr Asp Thr His His Val Glu Leu Ala Arg Glu Arg Ser Lys
            35                  40                  45

Thr Val Thr Ser Phe Tyr Asn Gln Ser Ala Ile Asp Val Val Ala Glu
50                  55                  60

Lys Pro Ser Val Arg Leu Thr Pro Thr Met Met Leu Tyr Ser Gly Arg
65                  70                  75                  80

Ser Gln Asp Gly Ser His Leu Leu Lys Ser Gly Arg Tyr Leu Gln Gln
                85                  90                  95

Glu Leu Pro Val Arg Ile Ala His Arg Ile Lys Gly Phe Val Val Phe
            100                 105                 110

Leu Ser Ser Leu Val Ala Thr Leu Pro Tyr Cys Thr Val His Glu Leu
            115                 120                 125

Tyr Ile Arg Ala Phe Gln Lys Leu Thr Asp Phe Pro Pro Ile Lys Asp
130                 135                 140

Gln Ala Asp Glu Ala Gln Tyr Cys Gln Leu Val Arg Gln Leu Leu Asp
145                 150                 155                 160

Asp His Lys Asp Val Val Thr Leu Leu Ala Glu Gly Leu Arg Glu Ser
                165                 170                 175

Arg Lys His Ile Glu Asp Glu Lys Leu Val Arg Tyr Phe Leu Asp Lys
            180                 185                 190

Thr Leu Thr Ser Arg Leu Gly Ile Arg Met Leu Ala Thr His His Leu
            195                 200                 205

Ala Leu His Glu Asp Lys Pro Asp Phe Val Gly Ile Ile Ser Thr Arg
210                 215                 220

Leu Ser Pro Lys Lys Ile Ile Glu Lys Trp Val Asp Phe Ala Arg Arg
225                 230                 235                 240

Leu Cys Glu His Lys Tyr Gly Asn Ala Pro Arg Val Arg Ile Asn Gly
                245                 250                 255

His Val Ala Ala Arg Phe Pro Phe Ile Pro Met Pro Leu Asp Tyr Ile
            260                 265                 270

Leu Pro Glu Leu Leu Lys Asn Ala Met Arg Ala Thr Met Glu Ser His
            275                 280                 285

Leu Asp Thr Pro Tyr Asn Val Pro Asp Val Val Ile Thr Ile Ala Asn
290                 295                 300

Asn Asp Val Asp Leu Ile Ile Arg Ile Ser Asp Arg Gly Gly Gly Ile
305                 310                 315                 320

Ala His Lys Asp Leu Asp Arg Val Met Asp Tyr His Phe Thr Thr Ala
                325                 330                 335

Glu Ala Ser Thr Gln Asp Pro Arg Ile Ser Pro Leu Phe Asp His Leu
            340                 345                 350

Asp Thr His Ser Gly Gly Gln Ser Gly Pro Met His Gly Phe Gly Phe
            355                 360                 365

Gly Leu Pro Thr Ser Arg Ala Tyr Ala Glu Tyr Leu Gly Gly Ser Leu
```

-continued

```
                      370                 375                 380
Gln Leu Gln Ser Leu Gln Gly Ile Gly Thr Asp Val Leu His Arg Ser
385                 390                 395                 400

Arg His Ile Asp Gly Arg Glu Glu Ser Phe Arg Ile
                405                 410

<210> SEQ ID NO 6
<211> LENGTH: 30
<212> TYPE: DNA
<213> ORGANISM: Primer

<400> SEQUENCE: 6
aggagagact cgaggcttat ggcagtgaag                                  30

<210> SEQ ID NO 7
<211> LENGTH: 5
<212> TYPE: PRT
<213> ORGANISM: Arabidopsis thaliana
<220> FEATURE:
<221> NAME/KEY: misc_feature
<223> OTHER INFORMATION: Xaa represents any amino acid

<400> SEQUENCE: 7

Gly Xaa Gly Xaa Gly
1               5

<210> SEQ ID NO 8
<211> LENGTH: 5
<212> TYPE: PRT
<213> ORGANISM: Arabidopsis thaliana
<220> FEATURE:
<221> NAME/KEY: misc_feature
<223> OTHER INFORMATION: Xaa represents any amino acid

<400> SEQUENCE: 8

Asp Xaa Gly Xaa Gly
1               5

<210> SEQ ID NO 9
<211> LENGTH: 9
<212> TYPE: PRT
<213> ORGANISM: Arabidopsis thaliana
<220> FEATURE:
<221> NAME/KEY: misc_feature
<223> OTHER INFORMATION: Xaa represents any amino acid

<400> SEQUENCE: 9

Glu Leu Xaa Lys Asn Xaa Xaa Arg Ala
1               5
```

PLANT PYRUVATE DEHYDROGENASE KINASE GENE

CROSS-REFERENCE TO RELATED APPLICATION

This application is a continuation of U.S. patent application Ser. No. 09/355,912, filed Oct. 15, 1999, now U.S. Pat. No. 6,500,670 the contents of which are incorporated by this reference, which itself claims priority from PCT International Application No. PCT/CA98/00096, (international filing date Feb. 9, 1998), designating the United States of America, and claiming priority from U.S. Provisional Patent Application No. 60/038,815, filed Feb. 10, 1997.

TECHNICAL FIELD

This invention relates to plant genes useful for the genetic manipulation of plant characteristics. More specifically, the invention relates to the identification, isolation and introduction of genes useful, for example, for altering the seed oil content, seed size, flowering and/or generation time, or vegetative growth of commercial or crop plants.

BACKGROUND

Through a coordination of the light and dark reactions of photosynthesis, plants assimilate $CO_2$ in the formation of sugars. Via the catabolic and anabolic reactions of metabolism, these sugars are the basis of plant growth, and ultimately plant productivity. In the process of plant growth, respiration, which involves the consumption of $O_2$ and catabolism of sugar or other substrates to produce $CO_2$, plays a central role in providing a source of energy, reducing equivalents and an array of intermediates (carbon skeletons) as the building blocks for many essential biosynthesic processes. It is known that any two plants with equal photosynthetic rates often differ in both total biomass production and harvestable product. Therefore, the relationship between rate of respiration and crop productivity has been one of the most intensively studied topics in plant physiology. In a biochemical sense, respiration can be taken to be composed of glycolysis, the oxidative pentose phosphate pathway, the Kreb's (tricarboxylic acid, TCA) cycle and the mitochondrial electron transport system. The intermediate products of respiration are necessary for growth in meristematic tissues, maintenance of existing phytomass, uptake of nutrients, and intra- and inter-cellular transport of organic and inorganic materials. In soybean there is evidence that an increase in respiration rate by the pod can lead to an increase in seed growth (Sinclair et al., 1987), while decreased respiration can result in decreased reproductive growth (Gale, 1974). Respiration is therefore important to both anabolic and catabolic phases of metabolism.

Although the pathways of carbon metabolism in plant cells are quite well known, control of the flux of carbon through these pathways in vivo is poorly understood at present. The mitochondrial pyruvate dehydrogenase complex (mtPDC), which catalyzes the oxidative decarboxylation of pyruvate to give acetyl CoA, is the primary entry point of carbohydrates into the Krebs cycle. The mtPDC complex links glycolytic carbon metabolism with the Krebs cycle, and, because of the irreversible nature of this reaction, the pyruvate dehydrogenase complex (PDC) is a particularly important site for regulation.

Mitochondrial PDC has been studied intensively in mammalian systems, and available knowledge about the molecular structure of plant mtPDC is largely based on studies of the mammalian mtPDC. The mtPDC contains the enzymes E1 (EC 1.2.4.1), E2 (EC 2.3.1.12) and E3 (EC 1.8.1.4) and their associated prosthetic groups, thiamine PPi, lipoic acid, and FAD, respectively. The E1 and E3 components are arranged around a core of E2. The E2 and E3 components are single polypeptide chains. In contrast, the E1 enzyme consists of two subunits, E1α and E1β. Their precise roles remain unclear. Another subunit, the E3-binding protein, is thought to play a role in attaching E3 to the E2 core. The E1 kinase and phosphatase are associated regulatory subunits (Grof et al., 1995).

Plants are unique in having PDH complexes in two isoforms, one located in the mitochondrial matrix as in other eukaryotic cells, and another located in the chloroplast or plastid stroma (Randall et al., 1989). Although both plastidial and mitochondrial PDH complex isoforms are very sensitive to product feedback regulation, only the mitochondrial PDH complex is regulated through inactivation/reactivation by reversible phosphorylation/dephosphorylation (Miernyk and Randall, 1987; Gemel and Randall, 1992; Grof et al., 1995). More specifically, the activity of mitochondrial PDC (mtPDC) is regulated through product feedback inhibition (NADH and acetyl-CoA) and the phosphorylation state of mtPDC is determined by the combined action of reversible phosphorylation of the E1α subunit by PDC kinase (PDCK) and its dephosphorylation by PDC phosphatase. PDCK phosphorylates and inactives PDC, while PDC phosphatase dephosphorylates and reactivates the complex. Maximum PDC activity also appears to vary developmentally, with the highest catalytic activity observed during seed germination and early seedling development (e.g., in post-germinative cotyledons, Hill et al., 1992; Grof et al., 1995).

Acetyl-CoA, the product of PDC, is also the primary substrate for fatty acid synthesis. While it is known that plant fatty acid biosynthesis occurs in plastids, the origin of the acetyl-CoA used for the synthesis of fatty acids in plastids has been the subject of much speculation. It remains a major question which has not been resolved. Because of the central role of acetyl-CoA in many metabolic pathways, it is likely that more than one pathway could contribute to maintaining the acetyl-CoA pool (Ohlrogge and Browse, 1995).

One school of thought takes the view that carbon for fatty acid synthesis is derived directly from the products of photosynthesis. In this scenario, 3-phosphoglycerate (3-PGA) would give rise to pyruvate, which would be converted to acetyl-CoA by pyruvate dehydrogenase in plastids (Liedvogel, 1986). This hypothesis has many appealing aspects, but also several unaddressed questions: (1) fatty acid synthesis occurs in photosynthetic (chloroplasts) and non-photosynthetic plastids (in root, developing embryo cotyledons, endosperm leucoplasts); (2) some plastids may lack 3-phosphoglycerate mutase (Kleinig and Liedvogel, 1980), an essential enzyme for converting 3-PGA, the immediate product of $CO_2$ fixation, to pyruvate. (3) Acetate is the preferred substrate for fatty acid synthesis using isolated intact plastids, and there is evidence that a multienzyme system including acetyl-CoA synthetase and acetyl-CoA carboxylase, exists in plastids, which channels acetate into lipids (Roughan and Ohlrogge, 1996). It is almost certain that at least some of the acetyl-CoA in plastids is formed by plastidic pyruvate dehydrogenase, using pyruvate imported from the cytosol or produced locally by plastidial glycolysis.

A further possibility, especially in non-photosynthetic tissues (e.g., roots and developing embryos), is that acetyl-CoA, generated in the mitochondria, is an alternate means to provide acetate moieties for fatty acid synthesis (Ohlrogge and Browse, 1995). Mitochondrially-generated acetyl-CoA could be hydrolysized to yield free acetate, which could move into the plastid for conversion to acetyl-CoA via plastidial acetyl-CoA synthetase, an enzyme with 5- to 15-fold higher activity than the in vivo rate of fatty acid synthesis (Roughan and Ohlrogge, 1994). Alternatively, the mitochondrial acetyl-CoA could be converted to acetylcarnitine and transported directly into the plastid. Hence, in theory, the mitochondrial pyruvate dehydrogenase complex has an important role to play in fatty acid biosynthesis (see FIG. 1 of the accompanying drawings). The proof of this hypothesis has been hindered by the difficulties of directly measuring the existence of acetate in the cytosol.

The mitochondrial PDC (mtPDC) is a tightly regulated mutiple subunit complex. As mentioned previously, one of the key regulatory components of this complex is PDH_ kinase (PDHK). PDHK functions as a negative regulator by inactivating PDH via phosphorylation. By modulating the PDCK, the activity of PDC can be genetically engineered.

Various attempts have been made to increase or channel additional carbon towards fatty acid biosynthesis. Targets have included genetically modifying acetyl-CoA carboxylase and pyruvate kinase gene expression through overexpression and antisense mRNA techniques with limited or no success.

However, there are many examples of successful modifications to plant metabolism that have been achieved by genetic engineering to transfer new genes or to alter the expression of exisiting genes, in plants. It is now routinely possible to introduce genes into many plant species of agronomic significance to improve crop performance (e.g., seed oil or tuber starch content/composition; meal improvement; herbicide, disease or insect resistance; heavy metal tolerance etc.) (Somerville, 1993; Kishore and Somerville, 1993; MacKenzie and Jain, 1997).

For example, increases in the proportions of some strategic fatty acids and in the quantities of seed oil have been achieved by the introduction of various fatty acid biosynthesis and acyltransferase genes in oilseed crops. These include the following demonstrations: Expression of an anti-sense construct to the stearoyl-ACP Δ9 desaturase in *Brassicaceae* led to an increase in the stearic acid content (Knutzon et al., 1992). Expression of a medium chain fatty acyl-ACP thioesterase from California Bay, in *Brassicaceae* was demonstrated to increase the lauric acid (12:0) content (Voelker et al., 1992; 1996). Expression of a Jojoba β keto-acyl-CoA synthase in low erucic acid *Brassicaceae* led to an increase the level of erucic acid (22:1); the effect following expression in high erucic acid cultivars was negligible (Lassner et al., 1996). Increased proportions of oleic acid in *Brassica napus* and in soybean have been achieved by silencing the microsomal FAD2 (Δ12) desaturase (Hitz et al., 1995; Kinney, 1995; 1997). Transformation of *Arabidopsis thaliana* and rapeseed (*B. napus*) with a yeast sn-2 acyltransferase resulted in seed oils with increased proportions of 22:1 and other very long-chain fatty acids and significant increases in seed oil content (Zou et al., 1997).

Starch deposition has also been altered by genetic engineering. By expression of a mutant *E. coli* glgC16 gene encoding an ADP glucose pyrophosphorylase in potato tubers, an increase in starch accumulation was achieved (Stark et al., 1992).

However, because a PDHK gene has not heretofore been cloned from any plant, until now, no genetic modifications have addressed the possibility of altering carbon flux, increasing fatty acid synthesis, oil content or seed size, altering flowering and/or generation time, vegetative growth, or plant respiration/productivity by modulating plant mitochondrial PDH activity.

DISCLOSURE OF INVENTION

An object of the invention is to identify, isolate and characterize a pyruvate dehydrogenase kinase (PDHK) (gene and cDNA) sequence from *Arabidopsis* and to utilize this sequence in the genetic manipulation of plants.

Another object of the invention is to provide a vector containing the full-length PDHK sequence or a significant portion of the PDHK sequence from *Arabidopsis*, in an anti-sense orientation under control of either a constitutive or a seed-specific promoter, for reintroducing into *Arabidopsis* or for introducing into other plants.

Another object of the invention is to provide a method to construct a vector containing the full-length PDHK sequence or a significant portion of the PDHK sequence from *Arabidopsis*, in a sense orientation under control of either a constitutive or a seed-specific promoter, for re-introducing into *Arabidopsis* or for introducing into other plants.

Another object of the invention is to provide a method of modifiying *Arabidopsis* and other plants to change their seed oil content.

Another object of the invention is to provide a method of modifiying *Arabidopsis* and other plants to change their average seed weight or size.

Another object of the invention is to provide a method of modifiying *Arabidopsis* and other plants to change their respiration rate during development.

Another object of the invention is to provide a method of modifiying *Arabidopsis* and other plants to change their vegetative growth characteristics.

Another object of the invention is to provide a method of modifiying *Arabidopsis* and other plants to change their flowering time or patterns of generative growth.

Yet another object of the invention is to provide a method of modifiying *Arabidopsis* and other plants to change the period required to reach seed maturity.

According to one aspect of the present invention, there is provided isolated and purified deoxyribonucleic acid (DNA) of SEQ ID NO:1 (pYA5; ATCC No 209562).

According to yet another object of the invention, there is provided a vector containing SEQ ID NO:1 or a part thereof, for introduction of the gene, in an anti-sense orientation (e.g., pAsYA5; ATCC No 209561) into a plant cell, and a method for preparing a vector containing SEQ ID NO:1 or a part thereof, for introduction of the gene in a sense orientation, into a plant cell.

The invention also relates to transgenic plants and plant seeds having a genome containing an introduced DNA sequence of SEQ ID NO:1 and a method of producing such plants and plant seeds.

The invention also relates to substantially homologous DNA sequences from plants with deduced amino acid sequences of 25% or greater identity, and 50% or greater similarity, isolated and/or characterized by known methods using the sequence information of SEQ ID NO:1, as will be appreciated by persons skilled in the art, and to parts of reduced length that are still able to function as inhibitors of gene expression by use in an anti-sense or co-suppression (Transwitch; Jorgensen and Napoli 1994) application. It will be appreciated by persons skilled in the art that small changes in the identities of nucleotides in a specific gene sequence may result in reduced or enhanced effectiveness of the genes and that, in some applications (e.g., anti-sense or co-suppression), partial sequences often work as effectively as full length versions. The ways in which the gene sequence can be varied or shortened are well known to persons skilled in the art, as are ways of testing the effectiveness of the altered genes. All such variations of the genes are therefore claimed as part of the present invention.

Stated more generally, the present invention relates to the isolation, purification and characterization of a mitochondrial pyruvate dehydrogenase kinase (PDHK) gene from the Brassicaceae (specifically Arabidopsis thaliana) and demonstrates its utility in regulating fatty acid synthesis, seed oil content, seed size/weight, flowering time, vegetative growth, respiration rate and generation time. Until now, no concrete data is available on the gene structure of plant PDC regulatory subunits (PDCK and PDC phosphatase).

The PDHK gene was cloned and characterized in the course of experiments designed to complement an E. coli mutant, JC201 (Coleman, 1990) with a plant (A. thaliana) cDNA library. By expressing the cDNA as a fusion protein in E. coli, its function was established as a PDHK in a protein kinase assay where it specifically phosphorylated the mammalian PDH E1α/E1β subunits (the specific substrates of PDHK). The A. thaliana PDHK structure is significantly homologous to its mammalian counterpart, particularly among the functional domains.

The PDHK of the invention is useful in manipulating PDH activity, and the respiration rate in plants. For example, by transforming plants with a construct containing the partial PDHK gene in an antisense or in a sense orientation, under the control of either constitutive or tissue-specific promoters, the expression of mitochondrial PDHK can be silenced to some degree by anti-sense or co-suppression (Transwitch) phenomena (De Lange et al., 1995; Mol et al., 1990; Jorgensen and Napoli, 1994; Kinney, 1995), respectively. This can result in increased mitochondrial PDH activity, and hence an increased production or availability of mitochondrially-generated acetyl-CoA, or an increased respiration rate.

Alternatively, by over-expressing the full-length PDHK gene selectively in a tissue-specific manner, the activity of mitochondrial PDH may be negatively regulated, resulting in decreased respiratory rates in tissues, such as leaves or tubers, to decrease maintenance respiration and thereby increase the accumulation of biomass.

Some of the manipulations and deliverables which are possible using the PDHK gene or a part therof, include, but are not limited to, the following: seeds with increased or decreased fatty acid and oil content; plants exhibiting early or delayed flowering times (measured in terms of days after planting or sowing seed); plants with increased or decreased vegetative growth (biomass); plants with root systems better able to withstand low soil temperatures or frost; plants with tissues exhibiting higher or lower rates of respiration; plants exhibiting an enhanced capacity to accumulate storage compounds in other storage organs (e.g., tubers); plants exhibiting an enhanced capacity to accumulate biopolymers which rely on acetyl moieties as precursors, such a polyhydroxyalkanoic acids or polyhydroxybutyric acids (Padgette et al., 1997).

BRIEF DESCRIPTION OF THE DRAWINGS

FIG. 2 shows the nucleotide sequence (SEQ ID NO:1) and the deduced amino acid sequence (SEQ ID NO:2) of the Arabidopsis thaliana PDH kinase (PDHK) cDNA (clone YA5; ATCC #209562).

FIG. 3 shows the amino acid sequence alignment of the Arabidopsis PDH kinase (Ya5p) (SEQ ID NO:2) with other mammalian mitochondrial ketoacid dehydrogenase kinases: Pdhk I, porcine PDH kinase subunit I (SEQ ID NO:3); Pdhk II, porcine PDH kinase subunit II (SEQ ID NO:4); and Bckdhk, porcine branched chain α-ketoacid dehydrogenase kinase (SEQ ID NO: 5). Dots indicate gaps. Identical amino acid residues are highlighted in bold upper case type.

FIGS. 7a, 7b, 7c and 7d show the results of experiments in which the YA5 PDHK cDNA was expressed as a fusion protein in *E. coli*. and tests conducted to confirm its function as a PDH Kinase. The YA5 cDNA was expressed as a fusion protein in *E. coli* as shown in FIG. 7a. Analysis by SDS-Polyacrylamide Gel Electrophoresis (SDS-PAGE) revealed that lysate of *E. coli* transformed with the *A. thaliana* PDHK (YA5) has a very strongly-induced fusion protein of $M_r \approx 45$ kDa (Å), which is the predicted mass of the *A. thaliana* PDHK gene fusion product (42 kD+3 kD His TAG). FIG. 7b shows the mammalian E1α/E1β PDH subunit complex (obtained courtesy of Dr. M. Patel at the University of Buffalo). The proteins have been co-expressed in *E. coli*, to provide a substrate to test the capacity of PDHK to phosphorylate the E1 subunit of the PDH complex. FIGS. 7c and 7d are autoradiograms of radioactive incorporation of $^{32}P$ (from $\gamma$-$^{32}$P-ATP) into the E1 subunit of the E1α/E1β PDH complex. The left hand panels of 7c and 7d show the time-dependent (incubation times of 2, 5, 10, 15, or 20 min) in vitro phosphorylation of the E1α/E1β PDH complex by the action of the plant PDHK (product of clone YA5 expressed in *E. coli*), confirming its function as a pyruvate dehydrogenase kinase the first cloned from plants. In FIG. 7c, the control reaction (right hand panel) contains YA5 lysate+control *E. coli* lysate without E1α/E1β substrate. There is no evidence of phosphorylation of the E1α/E1β complex. In FIG. 7d, the control reaction (right hand panel) contains control *E. coli* lysate (without YA5 insert)+the E1α/E1β substrate. Again, there is no evidence of phosphorylation of the E1α/E1β complex.

FIG. 13 shows the average number of rosette leaves present upon entering the generative phase, in *A. thaliana* non-transformed control (WT) plants, and the $T_2$ generation of pBI121 plasmid only control (pBI121) transgenics, and anti-sense pyruvate dehydrogenase kinase (PDHK) transgenics, designated as YA5 lines. The average number of rosette leaves per plant is reduced in *A. thaliana* YA5 lines transformed with a constitutively-expressed anti-sense PDHK construct, compared to non-transformed controls or transformants containing only the selectable marker gene (transformed with pBI121), but without anti-sense PDHK. The perturbed vegetative growth phase in the anti-sense PDHK transgenics (see, also, FIG. 12) correlates well with the earlier flowering phenotype (see also FIG. 11).

BEST MODES FOR CARRYING OUT THE INVENTION

Figure 1:
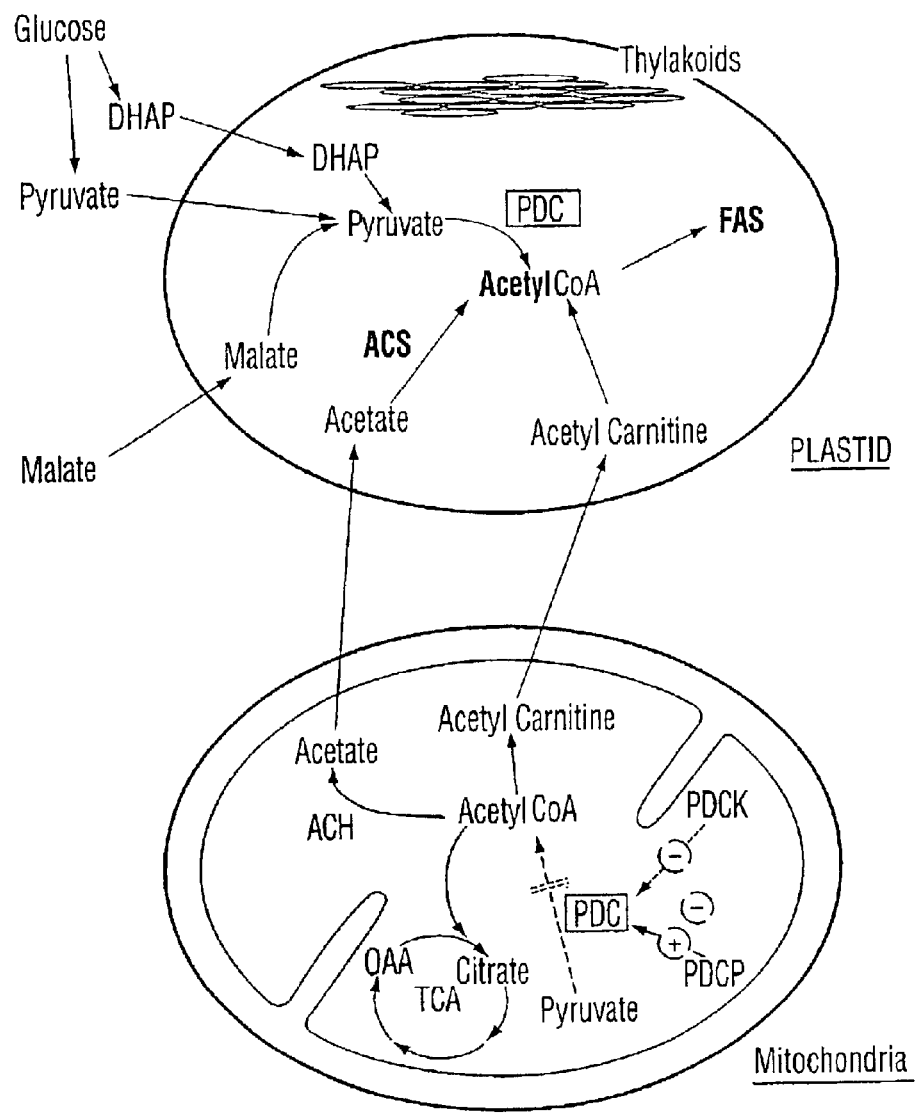
FIG. 1 shows the central role played by acetyl-CoA in mitochondrial respiration and plastidial fatty acid biosynthesis. The pyruvate dehydrogenase complex (PDC) oxidatively decarboxylates pyruvate to yield acetyl-CoA. Plants are unique in that they have both mitchondrial and plastidial isoforms of the PDC. The mitochondrial pyruvate dehydrogenase complex plays a key role in the regulation of acetyl-CoA generation and availability of acetyl moieties for various catabolic and anabolic reactions in plant cells. The mitochondrial PDC is negatively regulated by phosphorylation of the E1α subunit by pyruvate dehydrogenase kinase (PDCK=PDHK), and postively regulated by dephosphorylation of the PDC by pyruvate dehydrogenase phosphatase (PDCP). Mitochondrially-generated acetyl moieties can find their way into the respiratory tricarboxylic acid (TCA) cycle, but also into the plastid compartment where ultimately, acetate units are used by the enzymes of the fatty acid synthesis (FAS) pathway to synthesize fatty acids. These are eventually incorporated into membrane and also storage glycerolipids. Other abbreviations: PDC, pyruvate dehydrogenase complex; OAA, oxaloacetate; ACS, acetyl-CoA synthetase; ACH, acetyl-CoA hydrolase; DHAP, dihydroxyacetone phosphate.

The best modes for carrying out the invention are apparent from the following description of the results of tests and experiments that have been carried out by the inventors.

The inventors chose to use the well-accepted model plant system *Arabidopsis thaliana* for the cloning of PDHK, as a host system for genetic engineering to alter PDHK expression, and to study the effects of altering PDHK expression on various plant developmental and metabolic processes.

This is because over the past several years, *Arabidopsis thaliana*, a typical flowering plant, has gained increasing popularity as a model system for the study of plant biology. As a result of the ease with which this plant lends itself to work in both classical and molecular genetics, *Arabidopsis* has come to be widely used as a model organism in plant molecular genetics, development, physiology and biochemistry (Meyerowitz and Chang, 1985; Meyerowitz, 1987; Goodman et al., 1995). This model dicotyledonous plant is also closely related to Brassica crop species and it is increasingly apparent that information concerning the genetic control of basic biological processes in *Arabidopsis* will be transferable to other species (Lagercrantz et al., 1996).

Indeed, there are numerous examples wherein studies of the molecular biology and biochemistry of a particular metabolic pathway or developmental process and the possibility of genetically engineering a plant to bring about changes to said metabolic pathway or process, has first been tested in the model plant *Arabidopsis*, and then shown to yield similar phenotypes in other plants, particularly crop plants.

For example, the extra-plastidial membrane associated oleate (18:1) Δ12 (ω-6) desaturase gene, FAD2, was originally studied and eventually cloned from *Arabidopsis thaliana*, by identifying the lesion found in an *A. thaliana* mutant defective in desaturating oleate to produce linoleate (18:2) on the phosphatidylcholine backbone. This resulted in a high oleic acid phenotype in the *A. thaliana* seed oil (Okuley et al., 1994). Genetic engineering of both soybean (*Glycine max.*) and canola *B. napus* to silence the indigenous FAD2 gene(s) in a seed-specific manner by anti-sense or co-suppression approaches, resulted in similar high oleic acid seed oil phenotypes (Kinney, 1995; 1997).

Transgenic expression of a yeast sn-2 acyltransferase (SLC1-1) gene to achieve enhanced seed oil and very long-chain fatty acid content was first performed in *Arabidopsis* and later shown to yield similar phenotypes in transgenic rapeseed (*B. napus*) experiments (Zou et al., 1997). *Arabidopsis thaliana* has repeatedly shown itself to be a useful model system for metabolic engineering of metabolic pathways (e.g., lipid biosynthesis, photosynthesis) or processes (organogenesis, reproductive development etc.) common to all higher plants.

In the area of secondary metabolism/signal transduction, an anthocyanin pathway-specific transcriptional activator from the monocot maize designated as R (the myc transcription factor involved in activation of biosynthetic genes for anthocyanin production in the aleurone cells of maize kernels), was expressed in the dicot Arabidopsis, causing augmented anthocyanin pigmentation in the infloresecences. Subsequent expression in another dicot, tobacco (*Nicotiana tabacum*), resulted in similar floral pigmentation changes (Lloyd et al., 1992). These experiments demonstrate that whole pathways common to all flowering plants can be co-ordinately controlled through the introduction of transcriptional regulators, and that the mechanisms are common to diverse plant species.

In the context of the current invention, all plant cells undergo mitochondrial respiration and this ubiquitous process is affected by the activity of the PDC and its regulators PDCK and PDCP as explained previously. Thus, many of the effects observed following genetic engineering to modulate PDCK expression in *Arabidopsis* can be expected to result in similar phenotypes when carried out in all other plants.

There are a number of ways by which genes and gene constructs can be introduced into plants, and a combination of plant transformation and tissue culture techniques have been successfully integrated into effective strategies for creating transgenic crop plants. These methods, which can be used in the present invention, have been extensively reviewed elsewhere (Potrykus, 1991; Vasil, 1994; Walden and Wingender, 1995; Songstad et al., 1995), and are well known to persons skilled in the art. For example, one skilled in the art will certainly be aware that, in addition to Agrobacterium-mediated transformation of *Arabidopsis* by vacuum infiltration (Bechtold et al., 1993) or wound inoculation (Katavic et al., 1994), it is equally possible to transform other plant and crop species, using *Agrobacterium* Ti-plasmid-mediated transformation (e.g., hypocotyl (DeBlock et al., 1989) or cotyledonary petiole (Moloney et al, 1989) wound infection), particle bombardment/biolistic methods (Sanford et al., 1987; Nehra et al., 1994; Becker et al., 1994) or polyethylene glycol-assisted protoplast transformation (Rhodes et al., 1988; Shimamoto et al., 1989) methods.

As will also be apparent to persons skilled in the art, and as extensively reviewed elsewhere (Meyer, 1995; Datla et al., 1997), it is possible to utilize plant promoters to direct any intended up- or down-regulation of transgene expression using constitutive promoters (e.g., those based on CaMV35S), or by using promoters which can target gene expression to particular cells, tissues (e.g., napin promoter for expression of transgenes in developing seed cotyledons), organs (e.g., roots), to a particular developmental stage, or in response to a particular external stimulus (e.g., heat shock).

Particularly preferred plants for modification according to the present invention include borage (*Borago* spp.), Canola, castor (*Ricinus communis*), cocoa bean (*Theobroma cacao*), corn (*Zea mays*), cotton (*Gossypium* spp), *Crambe* spp., *Cuphea* spp., flax (*Linum* spp.), *Lesquerella* and *Limnanthes* spp., Linola, nasturtium (*Tropaeolum* spp.), *Oenothera* spp., olive (*Olea* spp.), palm (*Elaeis* spp.), peanut (*Arachis* spp.), rapeseed, safflower (*Carthamus* spp.), soybean (*Glycine* and *Soja* spp.), sunflower (*Helianthus* spp.), tobacco (*Nicotiana* spp.), *Vernonia* spp., wheat (*Triticum* spp.), barley (*Hordeum* spp.), rice (*Oryza* spp.), oat (*Avena* spp.) sorghum (*Sorghum* spp.), rye (*Secale* spp.) or other members of the *Gramineae*.

Results cDNA Cloning and Sequence Analysis of Clone YA5 (Plant PDHK).

A plant PDHK cDNA sequence designated YA5 was identified and cloned during experiments designed to complement an *E. coli* mutant JC201 (Coleman, 1990) with an *Arabidopsis thaliana* cDNA library. The *E. coli* mutant JC201 has been reported to be a mutant deficient in lysophosphatidic acid acyltransferase (LPAT; EC 2.3.1.51) activity, and possesses a temperature-sensitive growth phenotype (Coleman, 1990). Plasmids generated from an *A. thaliana* λ-YES expression library (Elledge et al., 1991) were used to transform *E. coli* mutant JC201. A restrictive temperature condition (44° C.) was applied to select surviving colonies. cDNAs were isolated from temperature-insensitive transformants. Clone YA5 was found to be able to complement or rescue the temperature-sensitivity of JC201, but no elevated LPAT activity could be detected in lysates of the transformant. Thus, the mechanism underlying the ability to complement the temperature sensitivity of JC201 remains unclear. However, several other complementing clones have also been found to rescue the temperature-sensitive phenotype of JC201, indicating that temperature complementation can occur upon transformation with cDNAs having functions unrelated to LPAT (Taylor et al., 1992a; Zou and Taylor, 1994).

The YA5 cDNA was sequenced from both strands on an Applied Biosystems Model 373A DNA Sequencing System using the Taq DyeDeoxy™ Terminator Cycle Sequencing Kit (Applied Biosystems, Inc.). The nucleotide sequence of the 1.457 kb YA5 cDNA (pYA5; ATCC 209562) (SEQ ID NO:1) and its deduced amino acid sequence (SEQ ID NO:2) are shown in FIG. 2. A sample of the YA5 cDNA (pYA5) was deposited on Dec. 18, 1997 at the American Type Culture Collection (ATCC) of 12301 Parklawn Drive, Rockville, Md. 20852, USA, under accession number ATCC 209562. The sequence revealed a 103 nucleotide 5' untranslated region, and a 235 nucleotide 3' untranslated region followed by a poly A tail. YA5 has an open reading frame of 1098 base pairs encoding a polypeptide of 366 amino acids, with a calculated molecular weight of 41.37 kDa. The sequences around the initiation codon AUG are in good agreement with the consensus sequences derived from other plant species (Lutcke et al., 1987). There is an in-frame stop codon upstream of the start codon, indicating that YA5 is a full-length cDNA. The calculated isoelectric point of the YA5 protein is 6.68 and its net charge at pH 7.0 is calculated to be −1.48.

Amino Acid Sequence Alignment

As shown in FIG. 3, comparisons of the deduced amino acid sequence (SEQ ID NO:2) of the YA5 protein (Ya5p) to the NCBI data bank revealed a high degree of homology with mammalian mitochondrial kinases responsible for phosphorylation and inactivation of α-ketoacid dehydrogenase complexes (Harris et al., 1992), including the pyruvate dehydrogenase complex (PDC), the α-ketoglutarate dehydrogenase complex (KGDC) and the branched-chain (α-ketoacid dehydrogenase complex (BCKDHC). These mammalian complexes are located in the mitochondrial matrix space (Damuni et al, 1984) and are similar in both structure and function (Nobukuni et al., 1990). cDNAs encoding the mammalian pyruvate dehydrogenase kinase (PDHK) and the branched-chain α-ketoacid dehydrogenase kinase (BCKDHK) have been cloned and the amino acid sequences of these protein kinases are highly homologous to each other (Popov et al., 1992; 1993; 1994).

The YA5 protein (Ya5p) is 28.6% identical and 83.7% similar to PDKI (Popov et al., 1993) and 32.3% identical and 88.4% similar to PDKII (Popov et al., 1994), both subunits of the porcine PDH kinase. Ya5p is also 28.8% identical and 84.1% similar to BCKDHK (Popov et al., 1992). The sequence similarity extends over the entire sequence, but sequence differences and alignment gaps occur throughout, particularly towards the amino and carboxyl termini.

SEQ ID NO:1 of the current invention and mammalian PDHK and BCKDHK do not exhibit significant homology with known serine/threonine protein kinases. Rather, a much higher degree of sequence homology was found with members of the prokaryotic protein histidine kinase family. As shown in FIG. 3, the most homologous regions fall into the conserved motifs defining histidine kinase functional domains. Members of the protein histidine kinase family have five regions that are highly conserved (Parkinson and Kofoid, 1992). All five motifs are easily identifiable in the YA5 deduced amino acid sequence, with the same order and spacing conserved in bacterial proteins. At the C-terminus, the catalytic domain (Block V) with a glycine-rich loop of $Gly^{320}$-X-$Gly^{322}$-X-$Gly^{324}$ (SEQ ID NO:7) as well as the sequence surrounding it, is the longest stretch of amino acids that exhibit high identity. Block III with the consensus sequence of $Asp^{278}$-X-$Gly^{280}$-X-$Gly^{282}$ (SEQ ID NO:8) characteristic of adenosine triphosphate (ATP)-binding proteins, and Block IV with an invariant $Phe^{292}$, are located at the positions defined as the central core of the catalytic domain. A highly-conserved region defined as Block II ($Glu^{238}$-Leu-X-Lys-$Asn^{242}$-X-X-Arg-$Ala^{246}$) (SEQ ID NO:9) of the catalytic domain is also found at the proper proximity to the N-terminus. The histidine residue ($His^{121}$) conserved among YA5, PDKI and PDKII would probably represent Block I, that is proposed to be involved in autophosphorylation.

Figure 4:
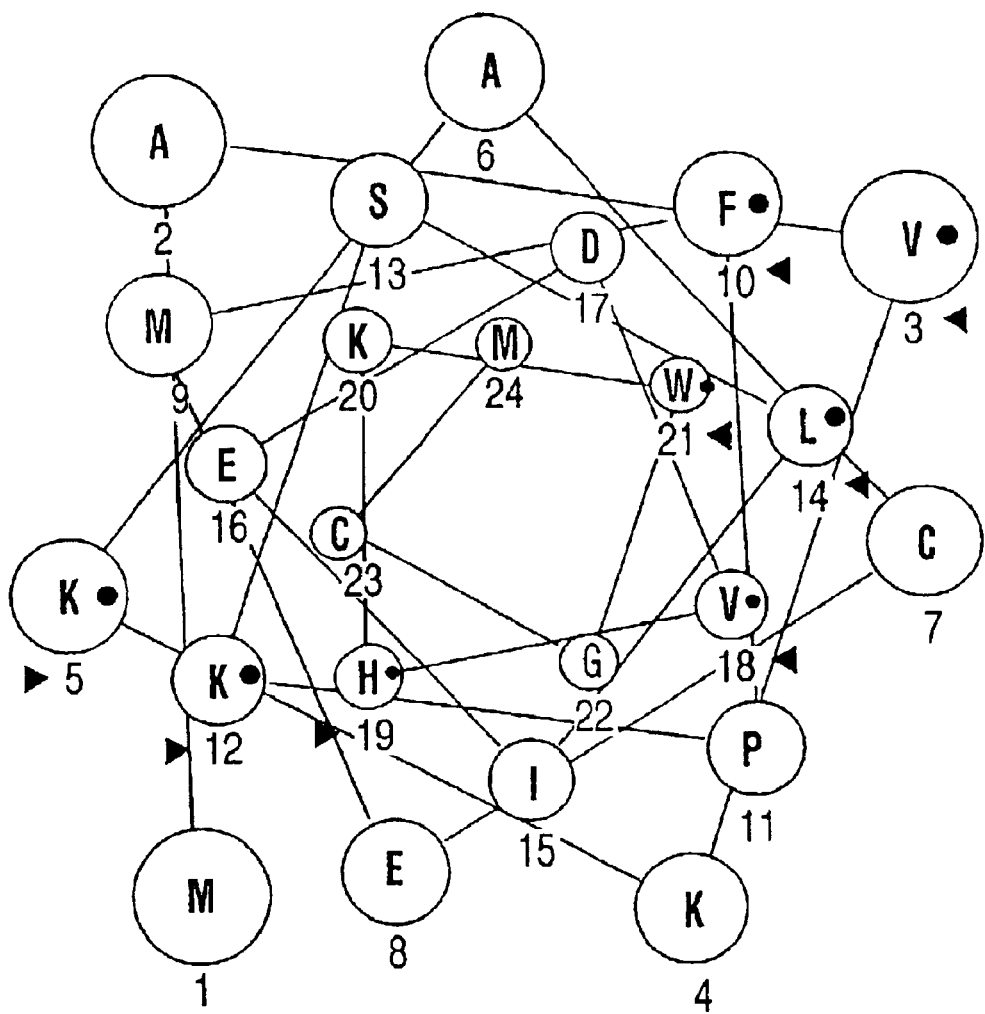
FIG. 4 shows the predicted helical wheel structure (angle=100°) of the 24 amino acid residues at the N-terminus of the YA5 (pyruvate dehydrogenase kinase, PDHK) protein. The N-terminal leader sequence of the YA5 protein corresponds well to most mitochondrial targeting sequences (Rosie and Schatz, 1988), consisting of a stretch of amino acids enriched in hydrophobic residues and opposing positively-charged residues. The key hydrophobic ($V_3$, $F_{10}$, $L_{14}$, $V_{18}$, and $W_{21}$) and positively-charged ($K_5$, $K_{12}$ and $H_{19}$) residues are found on opposing sides of the helical wheel motif in this mitochondrial targeting sequence, and are highlighted by • on the residue itself, and by Å next to the residue number.

The N-terminal leader sequence of the YA5 protein corresponds well to most mitochondrial targeting sequences (Rosie and Schatz, 1988), consisting of a stretch of amino acids enriched in hydrophobic and positively-charged residues, with a predicted helical wheel structure (angle= 100°) (FIG. 4). The key hydrophobic ($V_3$, $F_{10}$, $L_{14}$, $V_{18}$, and $W_{21}$) and positively-charged ($K_5$, $K_{12}$ and $H_{19}$) residues are found on opposing sides of the helical wheel motif in this mitochondrial targeting sequence. The YA5 protein lacks obvious targeting motifs typically found in proteins targeted to the peroxisomes (e.g., extreme C-terminus non-cleaved Ser-Lys-Leu (SKL) peroxisomal targeting sequence motif; Mullen et al., 1997).

Genomic Organization and Expression of the YA5 Gene in A. thaliana

Figure 5:
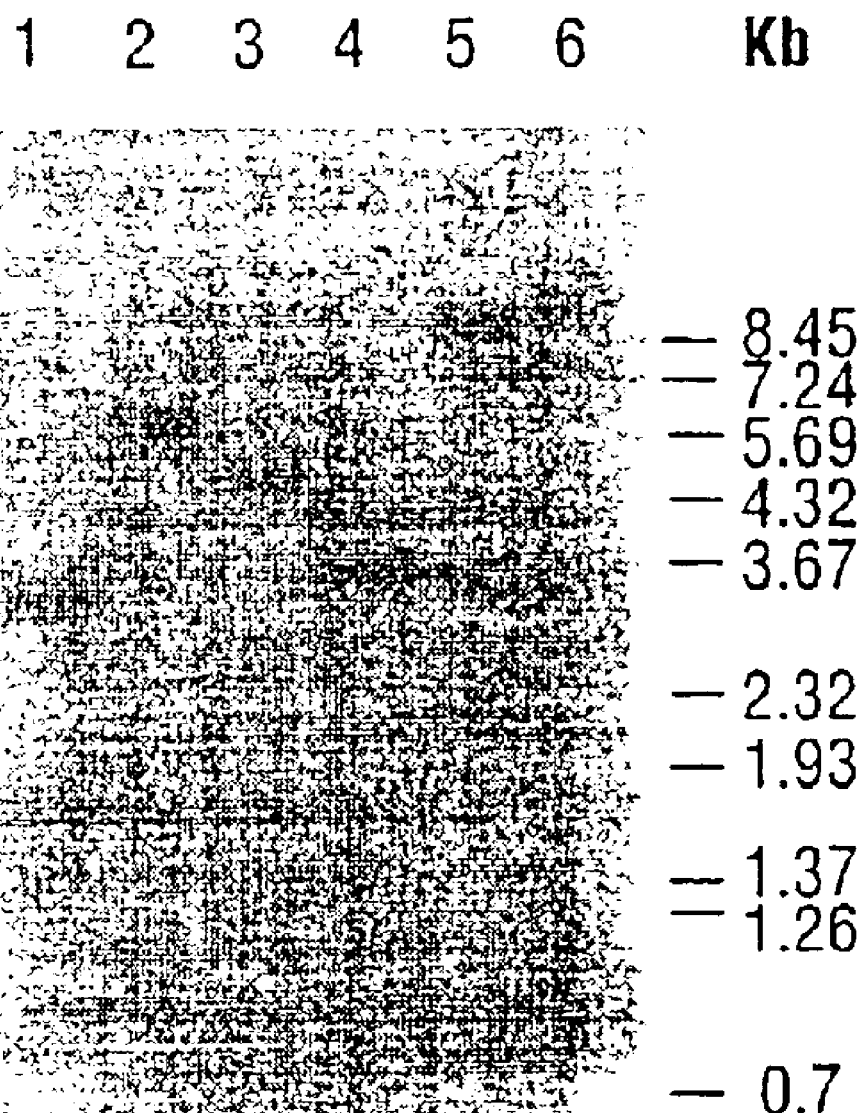
FIG. 5 shows the results of a DNA gel blot analysis (Southern, 1975) of the Arabidopsis thaliana YA5 (PDHK) gene. Genomic DNA was digested with PstI+XbaI (lane 1), XbaI (lane 2), PstI (lane 3), PvuII+SpeI (lane 4), SpeI (lane 5), and PvuII (lane 6). None of these enzymes has an internal restriction site on the YA5 (PDHK) cDNA. The digested DNA was hybridized with $^{32}$P-labeled YA5 cDNA (≈1.5 Kb) under high stringency conditions. All digests show only one hybridizing fragment suggesting that the PDHK gene most likely represents a single-copy gene in Arabidopsis thaliana.

Genomic DNA was digested with (XbaI+PstI), XbaI, PstI, (PvuII+SpeI), SpeI, and PvuII (there are no internal restriction sites on the YA5 cDNA for these enzymes). The digested DNA was then subjected to a DNA gel blot (Southern,1975) and hybridized with the $^{32}$P-labeled YA5 cDNA under high stringency hybridization conditions. As shown in FIG. 5, all of the digest reactions yielded only one hybridizing fragment (gel band), indicating that the YA5 gene most likely is present as a single copy in the Arabidopsis genome.

Figure 6:
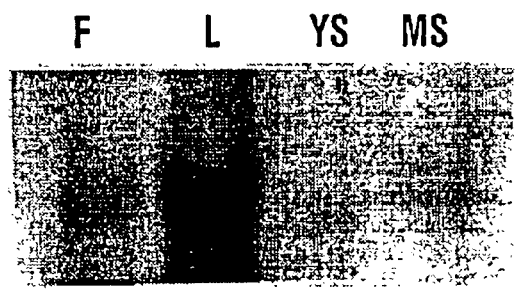
FIG. 6 depicts an RNA (northern) gel blot analysis of YA5 (PDHK) mRNA abundance/tissue distribution in A. thaliana. RNA was extracted from flowers (F), vegetative tissue (seedling leaves (L)), young developing siliques (YS) and maturing siliques (MS). The analysis shows that in all tissues, an RNA-hybridizing band of about 1.5 Kb was observed, but the abundance of the YA5 mRNA varied considerably from tissue to tissue. Young seedling leaves (L) showed the highest level of YA5 expression, while significant, but lower, levels of expression were observed in developing siliques (seeds).

To determine the relative abundance and tissue distribution of YA5 gene transcript, an RNA gel blot (northern blot) hybridization analysis, shown in FIG. 6, was performed on RNA extracted from A. thaliana seedlings, inflorescences (flowers), young siliques and maturing siliques. In all tissues, an RNA-hybridizing band of about 1.5 kb was observed, but the abundance of the YA5 mRNA varied considerably from tissue to tissue. Young seedlings showed the highest level of YA5 expression, while significant, but lower levels of expression were observed in developing siliques (seeds).

Expression of YA5 in E. coli and Confirmation of its Function as a PDH Kinase The YA5 full-length cDNA (YA5F) was cloned in pBluescript SK in a 5' to 3' orientation of T7-T3. A primer encompassing the putative translational initiation site OMpdk (AGGAGAGACTCGAGGCTTATGGCAGTGAAG) (SEQ ID NO:6) was synthesized to include a XhoI restriction site. Primer OMpdk and T3 primer were used in a PCR reaction to amplify the YA5 encoding region from YA5F. The resulting PCR fragment was digested with HindIII (HindIII site is present 3' to the stop codon) and XhoI and cloned into pTrcHisB vector (Clontech) to generate construct pZTa5. SDS-PAGE analysis with lysates from IPTG induced E. coli containing pZTa5 and pTrcHisB control vector (FIG. 7a), lanes 1 ("YA5") and 2 ("Control"), respectively), revealed that the pZTa5 transformant (FIG. 7a, lane 1 "YA5") exhibited a very strongly-induced fusion protein of $M_r \approx 45$ kD, which is the predicted mass of the A. thaliana PDHK gene fusion product ($\approx 42$ kD+3 kD His TAG).

Protein kinase activity of the E. coli expressed YA5 protein was assayed essentially as described by Liu et al., (1995). The protein phosphorylation substrates, human E1α and E1β co-expressed in, and purified from, E. coli M15, were obtained from Dr. M. S. Patel of the Department of Biochemistry, School of Medicine and Biomedical Sciences, State University of New York at Buffalo, Buffalo, N.Y. (FIG. 7b). This co-expressed E1α and E1β system has been used extensively in the study of the regulation of PDC $E_1$ phosphorylation in mammalian systems (Korotchkina and Patel, 1995). For phosphorylation experiments (shown in FIGS. 7c and 7d), 20–25 μg of E1α/E1β was combined with about 10 μg of YA5-accumulating E. coli cytosol protein in a final volume of 100 μL containing 20 mM potassium phosphate, pH 7.0, 1 mM magnesium chloride, 2 mM dithiothreitol, 0.1 mM EDTA and 200 μM cold ATP. The mixture was pre-incubated at room temperature for 5 minutes, and then 5 μCi $^{32}$P-γ-ATP was added to start the assay. After 2, 5, 10, 15 and 20 minutes, 20-μL aliquots were withdrawn and the reaction was stopped with 20 μL of SDS-denaturating mixture. Samples were separated on 10% SDS-PAGE and autoradiographed.

FIGS. 7c and 7d are autoradiograms of radioactive incorporation of $^{32}$P (from γ-$^{32}$P-ATP) into the E1 subunit of the E1α/E$^1$β complex. The left hand panels of 6(c) and 6(d) show the time-dependent (incubation times of 2, 5, 10, 15, or 20 min) in vitro phosphorylation of the E$_1$α/E$_1$β complex substrate by the action of the plant PDHK (clone YA5) fusion protein, confirming its function as a pyruvate dehydrogenase kinase, the first cloned from plants. In FIG. 7c the control reaction (right hand panel) contains YA5 lysate+ control E. coli lysate without PDH E1α/E1β substrate. There is no evidence of phosphorylation of the E1α/E1β substrate. In FIG. 7d, the control reaction (right hand panel) contains control E. coli lysate (without YA5 insert) +the E1α/E1β PDH complex substrate. There is no evidence of phosphorylation of the E1α/E1β complex in this control either.

Synthesis of YA5 Plant Transformation Constructs:

Anti-sense YA5 (Anti-sense PDHK) Construct for Constitutive Expression:

The YA5 cDNA contains internal BamHI (nt 628) and NcoI (nt 1176) restriction sites. The BamHI and NcoI fragment was freed from YA5F and cloned into the respective sites in pBI524 (Datla et al., 1993), in an anti-sense orientation, and located between the tandem cauliflower mosaic virus 35S promoter and the nopaline synthase terminator. The YA5 anti-sense cassette was then cut out from pBI524 by HindIII and EcoRI, and cloned into the respective sites of vector pRD400 (Datla et al., 1992). The final binary anti-sense vector pAsYA5/pRD400 (a sample of which was deposited on Dec. 18, 1997 under the terms of the Budapest Treaty at the American Type Culture Collection (ATCC) of 12301 Parklawn Drive, Rockville, Md. 20852, USA, under accession number ATCC 209561) was introduced into Agrobacterium tumefasciens strain GV3101 (bearing helper plasmid pMP90; Koncz and Schell, 1986) by electroporation.

Anti-Sense and Partial Sense YA5 (PDHK) Constructs for Seed-Specific Expression:

An 875 bp fragment of the YA5 cDNA was excised by a BamHI (Pharmacia) digestion and the fragment was ligated into plasmid pDH1, which contains the seed-specific napin promoter (pDH1 was kindly provided by Dr. P. S. Covello, NRC/PBI). The cassette and the insert (in either sense or anti-sense orientation) were excised by a partial digestion with HindIII and EcoRI, and the DNA fragments separated on agarose gels and purified using the Geneclean II Kit (Bio 101 Inc.). The fragments were then ligated into HindIII/EcoRI-digested pRD400. The final binary vectors pNAsYA5/pRD400 (anti-sense construct) or pNSYA5/pRD400 (partial sense construct), were introduced into Agrobacterium tumefasciens strain GV3101 (bearing helper plasmid pMP90; Koncz and Schell, 1986) by electroporation.

Constitutive Expression of Anti-Sense YA5 (Anti-sense PDHK) Gene in Arabidopsis thaliana:

Agrobacterium containing the pAsYA5/pRD400 was used to transform Arabidopsis by vacuum infiltration (Bechtold et al., 1993). In addition, it will be apparent to persons skilled in the art that transformation of Arabidopsis can also be achieved by wound inoculation (Katavic et al., 1994). Similarly, one skilled in the art will certainly be aware that transformation of other plant species is possible using Agrobacterium Ti-plasmid-mediated transformation (e.g., hypocotyl (DeBlock et al., 1989) or cotyledonary petiole (Moloney et al, 1989) wound infection), particle bombardment/biolistic methods (Sanford et al., 1987; Nehra et al., 1994; Becker et al., 1994) or polyethylene glycol-assisted protoplast transformation (Rhodes et al., 1988; Shimamoto et al., 1989) methods. Constructs may be driven by constitutive or tissue-specific (e.g., seed, root etc.) promoters, as will also be apparent to persons skilled in the art.

As controls, plants were either non-transformed (nt), or transformed with pBI121 vector only (Jefferson et al., 1987; without antisense-PDHK insert but containing the kanamycin selection marker and the β-glucuronidase reporter gene). Control and transgenic plants were grown at the same time under identical conditions in growth chambers as described by Katavic et al., 1995.

Results of DNA gel blot (Southern, 1975) analyses confirmed that all of the anti-sense PDHK transgenic lines (designated as YA5 lines 23, 31, 32, 52, 95, 104) have at least one insert per genome for the PDHK gene in an anti-sense orientation. As expected, the non-transformed wild type control and pBI121 (plasmid only) transgenic control have only one insert per genome, consistent with the original Southern analysis (see FIG. 5).

Figure 8:
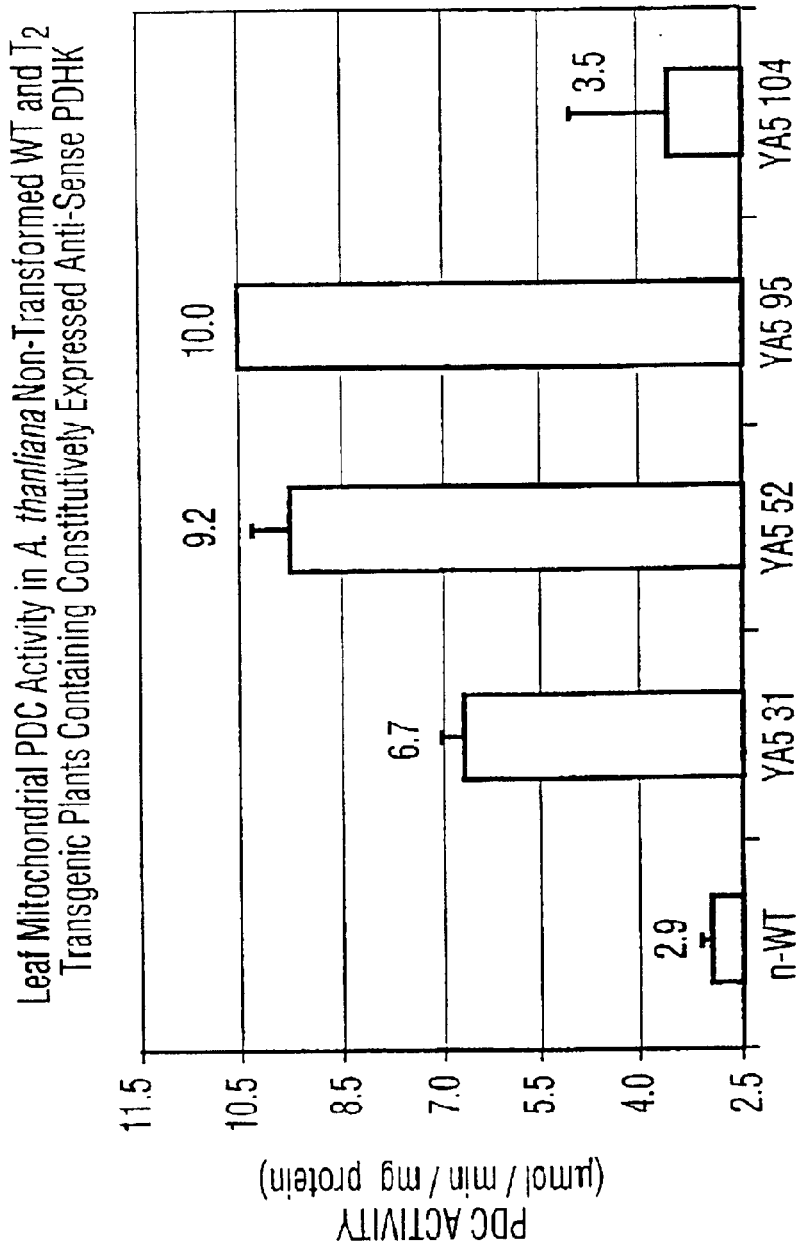
FIG. 8 shows the mitochondrial pyruvate dehydrogenase (PDC) activity in leaves from *A. thaliana* non-transformed wild-type (n-WT) plants and $T_2$ transgenic plants containing constitutively expressed anti-sense pyruvate dehydrogenase kinase (PDHK), designated as YA5 lines. Mitochondria isolated from leaves of *A. thaliana* YA5 transgenic lines containing a constitutively-expressed anti-sense PDHK construct, have elevated activity of PDC compared to mitochondria isolated from leaves of non-transformed control plants.

Analysis of Pyruvate Dehydrogenase (PDH) Activity in Mitochondria Isolated from A. thaliana Anti-Sense PDHK Transgenic Plants Shoot tissue was collected from A. thaliana transgenic plants containing the anti-sense PDHK construct, and from non-transformed control plants, and intact mitochondria were isolated. Pyruvate dehydrogenase (PDH) activity was determined by the method of Reid et al., (1977). As shown in FIG. 8, the PDH activity in mitochondria isolated from leaves of anti-sense PDHK transgenic plants was elevated by 20 to 350%, compared to PDH activity in mitochondria isolated from non-transformed controls.

Figure 9:
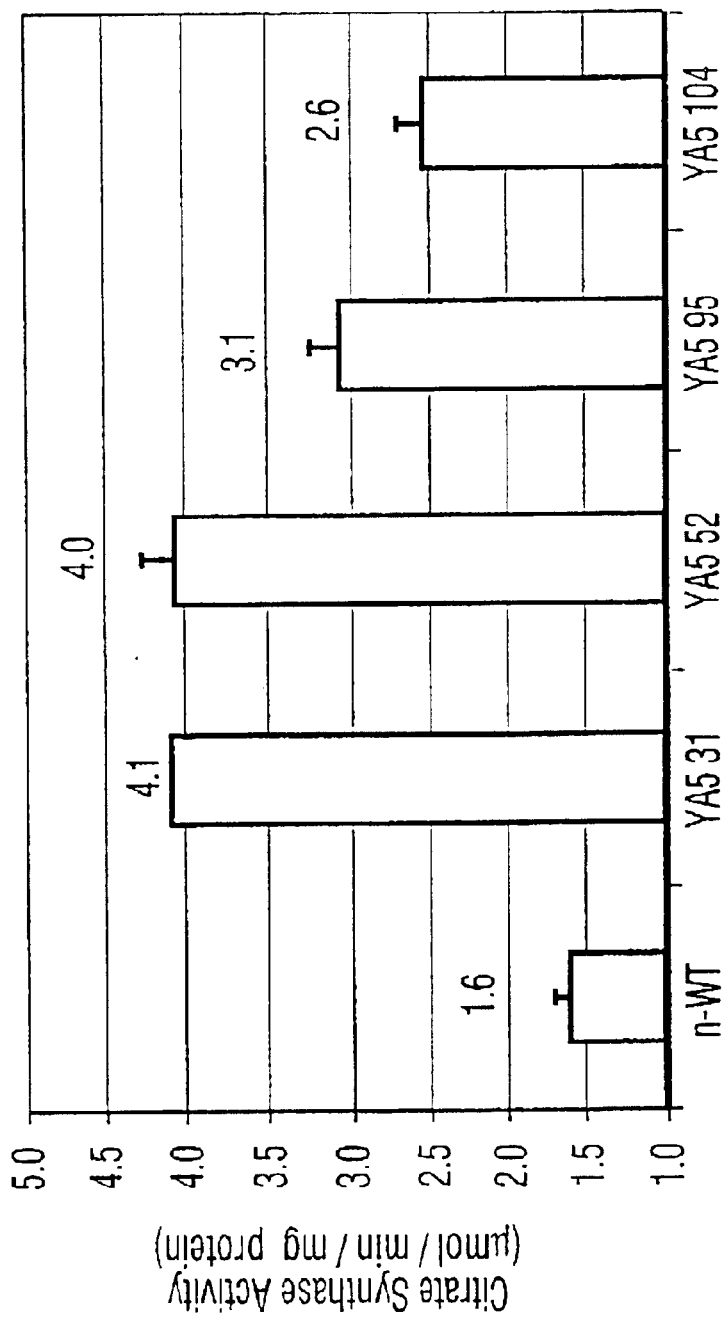
FIG. 9 shows the mitochondrial citrate synthase activity in leaves from *A. thaliana* non-transformed wild-type (n-WT) plants and $T_2$ transgenic plants containing constitutively expressed anti-sense pyruvate dehydrogenase kinase (PDHK), designated as YA5 lines. Mitochondria isolated from leaves of *A. thaliana* transgenic lines transformed with a constitutively-expressed anti-sense PDHK construct also have elevated activities of citrate synthase, in addition to elevated PDC, compared to mitochondria isolated from leaves of non-transformed control plants.

Analysis of Kreb's Cycle Enzyme Activities in Mitochondria Isolated from A. thaliana Anti-Sense PDHK Transgenic Plants The activities of the Kreb's Cycle enzymes citrate synthase, fumarase and succinate dehydrogenase were all significantly elevated in mitochondria isolated from leaves of anti-sense PDHK transgenic plants, compared to the respective activities in mitochondria isolated from non-transformed wild-type (n-WT) controls. Citrate synthase activites were about 160–240% higher (FIG. 9), while fumarase activites were about 65–120% higher, and succinate dehydrogenase activities were about 1014 65% higher in the anti-sense PDHK transgenics, compared to the corresponding n-WT activities set at 100%. These results suggest that mitochondrial respiration is increased in the anti-sense PDHK transgenics due to an increased availability of acetyl-CoA generated by enhanced PDC activity (due to down regulation of expression of PDHK, a negative regulator of PDC).

Analysis of Fatty Acid Composition and Content of Oils, and Average Seed Weights in T$_2$ Seeds from A. thaliana Anti-Sense PDHK and pBI121 Control Transgenic Plan Mature siliques and seeds were isolated from anti-sense PDHK transformants and from controls, either non-transformed or pBI121 transformants (without anti-sense PDHK, but with a kanamycin resistance gene), and the respective oil contents, fatty acyl compositions of the seed oils, average seed weights and number of siliques per 15 cm segment of stem were determined.

Figure 10:
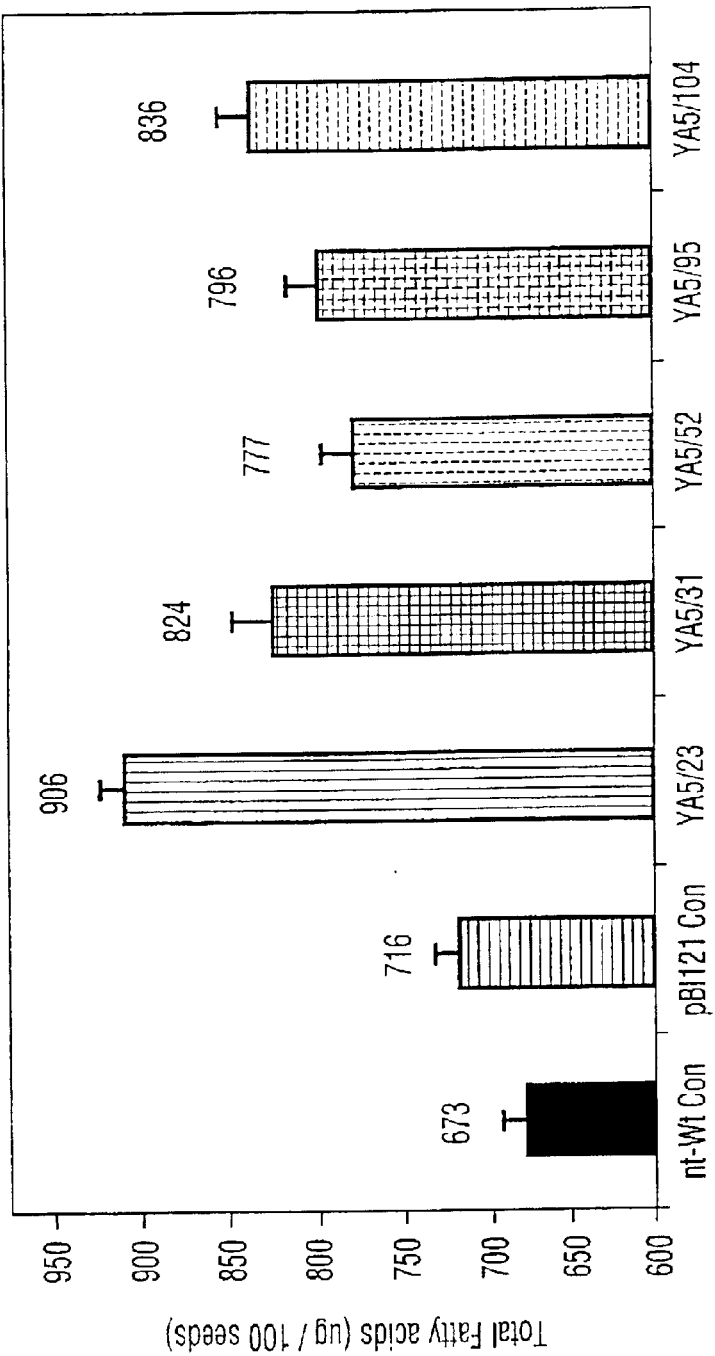
FIG. 10 shows the oil content (expressed as μg total fatty acids per 100 seeds) in seeds isolated from *A. thaliana* non-transformed controls (nt-WT Con), and $T_2$ seeds of pBI121 plasmid only control (pBI121 Con) transgenics, and anti-sense pyruvate dehydrogenase kinase (PDHK) transgenics, designated as YA5 lines. The *A. thaliana* YA5 seed lines transformed with a constitutively-expressed anti-sense PDHK construct have elevated fatty acid and oil content compared to seeds from non-transformed control plants or transformants containing only the selectable marker gene (transformed with pBI121), but without anti-sense PDHK.
Figure 11:
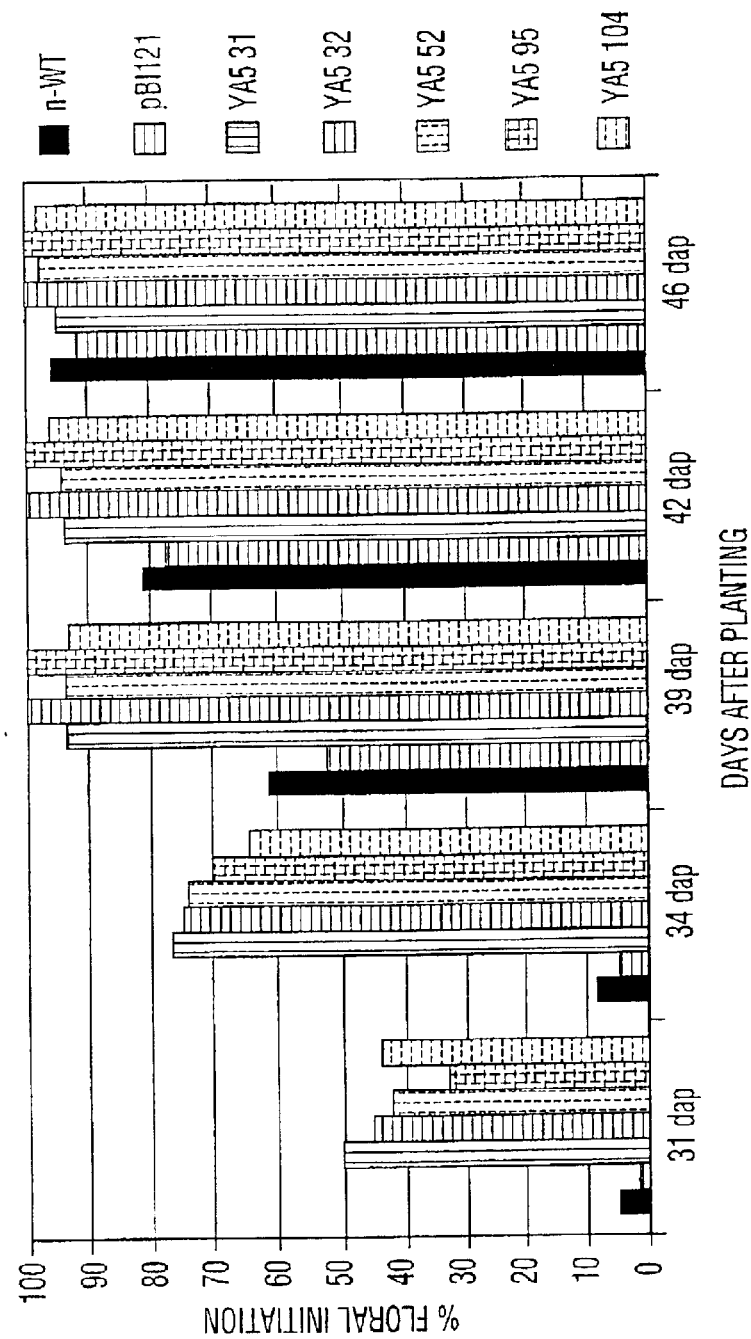
FIG. 11 shows the time (expressed in days after planting) to reach the flower initiation (generative) phase in *A. thaliana* non-transformed controls (nt-WT), and the $T_2$ generation of pBI121 plasmid only control (pBI121) transgenics, and anti-sense pyruvate dehydrogenase kinase (PDHK) transgenics, designated as YA5 lines. The time to reach the generative (floral initiation) stage is reduced in *A. thaliana* YA5 lines transformed with a constitutively-expressed anti-sense PDHK construct, compared to non-transformed controls or transformants containing only the selectable marker gene (transformed with pBI121), but without anti-sense PDHK.

As shown in FIG. 10, overall oil content, expressed as μg total fatty acids/100 seeds, was significantly elevated in the anti-sense PDHK transformants, by 8.5–26.5%, and by 15.4–34.6%, compared to pBI121 transformants and non-transformed controls, respectively. This indicated that overall flux of acetyl moieties into seed storage lipids was enhanced by a greater contribution from mitochondrially-generated acetate. The latter was enabled by increased mitochondrial PDH activity, due to the down-regulation of the negative regulator PDHK, in the antisense PDHK transformants.

Table 1 shows the oil content and average weight of seeds isolated from *A. thaliana* lines transformed with a constitutively-expressed anti-sense PDHK construct in comparison with seeds of plasmid only (pBI121) transformants and non-transformed controls. Both the amount of oil and the average seed weight are higher in the anti-sense PDHK transformants.

TABLE 1

Mean seed oil content and seed weight in non-transformed controls and $T_2$ seed of pBI121 control and anti-sense YA5 (A/S PDHK) transgenic plants.

| A. thaliana line | Seed Oil Content (mg oil/400 seeds) | Seed Weight (mg/400 seeds) |
| --- | --- | --- |
| Non-transformed Control | 3.13 | 7.40 |
| pBI121 (plasmid only) Control | 3.30 | 7.21 |
| A/S YA5 31 | 3.89 | 9.02 |
| A/S YA5 32 | 3.66 | 8.55 |
| A/S YA5 52 | 3.75 | 8.61 |
| A/S YA5 95 | 3.68 | 8.70 |
| A/S YA5 104 | 3.87 | 8.83 |

The average number of siliques per 15 cm segment of bolted stem was not significantly affected in the *A. thaliana* lines transformed with a constitutively-expressed anti-sense PDHK construct (designated as YA5 lines), in comparison with plasmid only (pBI121) transformants and non-transformed control plants. Following propagation of the $T_2$ generation of seed, non-transformed wild-type and pBI121 control transgenic *A. thaliana* plants produced 30±3 siliques and 31±4 siliques, respectively, per 15 cm segment of bolted stem. The anti-sense PDHK transgenic YA5 lines 31, 32, 52, 95 and 104 produced 26±3, 27±3, 27±3, 26±3, and 24±3 siliques per 15 cm segment of bolted stem, respectively.

The average number of $T_3$ seeds per silique was also not significantly affected. For example, the pBI121 control transformant produced 49.4±6.6 $T_3$ seeds per silique, and the anti-sense PDHK line YA 95 produced 50.1±8.5 $T_3$ seeds per silique (n=5–6 mature siliques sampled from 4 individual transgenic plants of each line). This indicated that seed yield (harvest index) was not adversely affected in the anti-sense PDHK transformants.

Table 2 shows the fatty acyl composition of seed oils isolated from *A. thaliana* lines transformed with a constitutively-expressed anti-sense PDHK construct in comparison with oil from seeds of plasmid only (pBI121) transformants and non-transformed controls. The antisense PDHK construct affects a point very early in the fatty acid biosynthesis/lipid bioassembly pathway, i.e., it enables a greater availability of acetyl moieties for plastidial fatty acid biosynthesis. Thus, while total flux of carbon through the lipid pathway into storage lipids was enhanced in seeds of the anti-sense PDHK transgenic plants, the fatty acyl composition of the oils which accumulated was not markedly changed (Table 2).

TABLE 2

Acyl composition of oils from seed of non-transformed controls (n-WT Control) and $T_2$ seed of pBI121 control (pBI121 Control) and Anti-Sense PDHK (A/S YA5) transgenic plants

| Sample | 16:0 | 18:0 | 18:1 c9 + c11 | 18:2 | 18:3 | 20:0 | 20:1 c11 + c13 | 20:2 | 22:0 | 22:1 c13 + c15 | 22:2 | 24:0 | 24:1 |
| --- | --- | --- | --- | --- | --- | --- | --- | --- | --- | --- | --- | --- | --- |
| n-WT Control | 7.5 (0.2)* | 3.5 (0.2) | 14.9 (0.2) | 27.0 (0.06) | 20.1 (0.04) | 1.9 (0.03) | 20.4 (0.1) | 2.2 (0.06) | 0.4 (0.1) | 1.9 (0.1) | 0.1 (0.1) | 0.1 (0.1) | 0.1 (0.1) |
| pBI121 Control | 7.7 (0.01) | 3.4 (0.02) | 15.5 (0.1) | 27.3 (0.2) | 19.8 (0.2) | 1.8 (0.0) | 19.8 (0.1) | 2.2 (0.03) | 0.3 (0.1) | 1.7 (0.1) | 0.2 (0.2) | 0.2 (0.2) | 0.1 (0.1) |
| A/S YA5 23 | 7.7 (0.0) | 3.6 (0.04) | 16.0 (1.0) | 27.5 (0.2) | 17.4 (0.3) | 2.3 (0.1) | 20.6 (0.3) | 2.1 (0.01) | 0.4 (0.1) | 2.0 (0.4) | 0.2 (0.2) | 0.3 (0.1) | 0.2 (0.01) |
| A/S YA5 31 | 7.9 (0.1) | 3.6 (0.1) | 15.7 (0.02) | 27.7 (0.02) | 17.5 (0.01) | 2.3 (0.02) | 20.3 (0.1) | 2.2 (0.02) | 0.4 (0.1) | 1.8 (0.02) | 0.2 (0.2) | 0.3 (0.03) | 0.2 (0.04) |
| A/S YA5 52 | 7.9 (0.02) | 3.6 (0.01) | 15.7 (0.1) | 27.6 (0.04) | 17.7 (0.1) | 2.3 (0.04) | 20.3 (0.2) | 2.2 (0.02) | 0.4 (0.1) | 1.9 (0.2) | 0.1 (0.1) | 0.1 (0.1) | 0.1 (0.1) |
| A/S YA5 95 | 8.0 (0.0) | 3.7 (0.1) | 15.5 (0.2) | 27.6 (0.3) | 17.7 (0.1) | 2.3 (0.04) | 20.3 (0.4) | 2.2 (0.1) | 0.5 (0.1) | 1.9 (0.3) | 0.2 (0.2) | 0.2 (0.2) | 0.1 (0.1) |
| A/S YA5 104 | 8.0 (0.01) | 3.8 (0.0) | 15.6 (0.02) | 27.7 (0.4) | 17.8 (0.02) | 2.4 (0.0) | 20.3 (0.04) | 2.1 (0.0) | 0.4 (0.1) | 1.7 (0.03) | 0.1 (0.1) | 0.2 (0.2) | 0.1 (0.1) |

*± SD (n = 2)

Analysis of Flowering Times of *A. thaliana* Anti-Sense PDHK and pBI121 Control Transgenic Plants The anti-sense PDHK transgenic plants displayed a significantly earlier transition from the vegetative to the generative phase of growth, i.e., earlier initiation of the generative (flower formation) phase (recorded by monitoring the time, as days after planting: d.a.p.) compared to non-transformed wild-type and pBI121 plasmid only controls. As shown in FIG. 11, 30-50% of the anti-sense PDHK transgenics were flowering as early as 31 d.a.p. compared to only 1-4% in the controls. This early flowering phenotype was even more dramatic at 34 d.a.p. when 50-75% of the anti-sense PDHK plants were in the generative phase compared to only 4-8% of the control plants. Most of the anti-sense PDHK plants were fully flowering (90% or greater floral initiation) by 39 d.a.p., but the non-transformed control plants and pBI121 plasmid only controls plants did not reach this stage until 46 d.a.p.

The time to reach maturity was also shorter in the anti-sense PDHK *A. thaliana* transgenics. For example, at 68 days after planting, all of the anti-sense PDHK transgenic lines had fully developed siliques and more than half of these were browned and mature. The few flowers that remained were senescing by this time. In contrast, the non-transformed wild type control plants and pBI121 control transformants still had significant flower development, primarily green immature siliques and only a few siliques which were brown and mature at this time. Under the growth conditions used by the inventors, the difference in maturity time was about 68–70 days for the anti-sense PDHK transgenic lines, compared to about 75–77 days for the control plants.

Given that the generation time in *Arabidopsis* control plants is about 75 days under the growth conditions used by the inventors, a 5 to 8-day earlier flowering and earlier maturing phenotype in the anti-sense PDHK plants represents a shortening of generation time by about 10%. Similar modification of flowering time to extend the geographical range of cultivation is an important goal for Brassica crops (Lagercrantz et al., 1996). In related *Brassicaceae* (e.g., Canola), this would allow the advantage of an earlier harvest (e.g., on the Canadian Prairies) and permit more northerly cultivation (Murphy and Scarth, 1994). Late season frost damage in temperate climates could be avoided by earlier maturity, and this could also significantly alleviate problems associated with late-season clearing of chlorophyll from the maturing seeds (which can lead to "green oil" during processing and necessitate expensive bleaching steps).

The inventors' data demonstrates that increased respiration can hasten the transition from the vegetative to the generative phase of plant growth. It is interesting to note that the opposite effect, i.e., a delay in flowering time, was observed in transgenic plants in which citrate synthase was down-regulated by anti-sense technology, which resulted in a decreased rate of respiration in vegetative tissues (Landschütze et al., 1995). Thus, flowering time can be hastened by increased respiration and delayed by reduced respiration.

Figure 12:
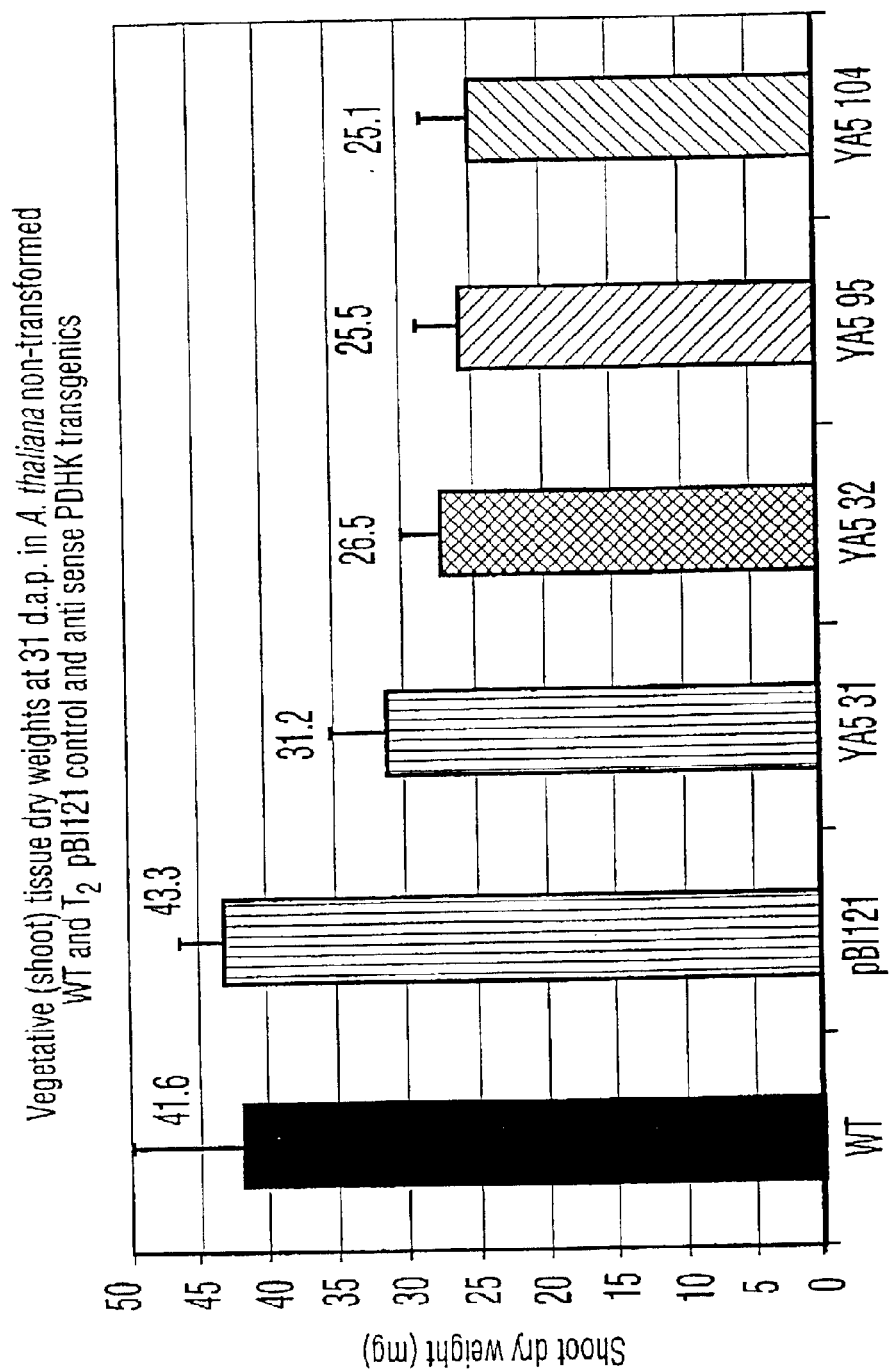
FIG. 12 shows vegetative shoot tissue dry weights at 31 days after planting in *A. thaliana* non-transformed controls (WT), and the $T_2$ generation of pBI121 plasmid only control (pBI121) transgenics, and anti-sense pyruvate dehydrogenase kinase (PDHK) transgenics, designated as YA5 lines. Shoot tissue growth is reduced in *A. thaliana* YA5 lines transformed with a constitutively-expressed anti-sense PDHK construct, compared to non-transformed controls or transformants containing only the selectable marker gene (transformed with pBI121), but without anti-sense PDHK.

Analysis of Vegetative Growth of *A. thaliana* Anti-Sense PDHK and pBI121 Control Transgenic Plants The earlier-flowering phenotype of the anti-sense PDHK transgenics was correlated with an altered pattern of vegetative growth. There was a reduced accumulation of vegetative shoot tissue mass (FIG. 12) correlated with a reduced number of rosette leaves produced in the anti-sense PDHK transgenics by the time plants switched to the generative (floral initiation) phase of growth (FIG. 13).

To summarize, *A. thaliana* lines transformed with a constitutively-expressed anti-sense PDHK construct (designated as YA5 lines) exhibit both altered vegetative growth and early flowering phenotypes, compared to the non-transformed controls or transformants containing only the selectable marker gene (transformed with pBI121), but without anti-sense PDHK. The difference with respect to the altered vegetative growth pattern phenotype of the anti-sense PDHK (YA5) transgenics (smaller plantlets with fewer rosette leaves compared to n-WT and pBI121 controls) was clearly visible at about 3.5 weeks after planting, and even more evident about one week later (30–31 days after planting). By about 31 days after planting, the early flowering phenotype was also apparent in the YA5 anti-sense PDHK transgenic lines. Many of the plants were beginning to bolt or show visible floral meristem (flower bud) initiation, while there was no evidence of such development in the n-WT and pBI121 controls. At 40 to 42 days after planting, the early flowering phenotype of the YA5 anti-sense PDHK transgenic lines was very apparent, with most or all transgenics fully bolted with open flowers, while the n-WT and pBI121 controls show a much lower frequency of bolting.

Whereas flowering and generation time were shortened in the YA5 lines, the average number of siliques, seed weight and oil content were not adversely affected. Rather, as shown in Table 1 and FIG. 10, both average seed weight and fatty acid/oil content per seed were enhanced in the YA5 lines.

Experimental Procedures

General Molecular Biological Techniques:

Isolation of plasmid DNA, restriction digestions, modification and ligation of DNA, PCR, agarose and polyacrylamide gel electrophoresis, transformation and culture of *E. coli* strains, DNA gel blot analyses (Southern, 1975) and RNA gel blot analyses, were carried out according to standard procedures as outlined by Sambrook et al., (1989).

Cloning of YA5:

An *Arabidopsis thaliana* (ecotype Columbia) λYES cDNA expression library (Elledge et al., 1991) was obtained from Dr. Ronald Davis (Dept. of Biochemistry, Stanford University School of Medicine, Stanford Calif. 94305). Plasmids were generated by automatic subcloning procedures as described by Elledge et al. (1991). A putative *Escherichia coli* lyso-phosphatidic acid acyltransferase (LPAT, EC 2.3.1.51) mutant, JC201 (Coleman 1990) was obtained from Dr. Jack Coleman (Dept. of Biochemistry and Molecular Biology, Louisiana State University Medical Center, New Orleans, La. 70112). JC201 was transformed with the plasmids generated from the λYES library, and selected at the non-permissive temperature of 44° C. (Coleman, 1992). The YA5 cDNA from the temperature-insensitive transformant was sequenced on an Applied Biosystems Model 373A DNA Sequencing System using the Taq DyeDeoxy™ Terminator Cycle Sequencing Kit (Applied Biosystems, Inc.). The nucleotide and deduced amino acid sequences of clone YA5 were compared with sequences available in data banks using the FASTA program (Pearson and Lipman, 1988).

Expression of the YA5 Protein in *E. coli*:

The YA5 full-length cDNA (YA5F) was cloned in pBluescript SK (+/−) in a 5' to 3' orientation of T7-T3. A primer encompassing the putative translational initiation site OMpdk (AGGAGAGACTCGAGGCTTATGGCA-GTGAAG) (SEQ ID NO:6) was synthesized to include an XhoI restriction site. Primer OMpdk and a T3 primer were used in a PCR reaction to amplify the YA5 encoding region from YA5F. The resulting PCR fragment was digested with HindIII (HindIII site is present 3' to the stop codon) and XhoI, and cloned into pTrcHisB vector (Clontech) to generate construct pZTa5. SDS-PAGE analysis with lysates from IPTG-induced *E. coli* containing pZTa5 and pTrcHisB control vector confirmed that a novel protein of approximately 45 kDa was synthesized.

Protein Kinase Assay with YA5-Expressing *E. coli* Lysate:

Protein kinase activity of the *E. coli* expressed YA5 protein was assayed essentially the same as described (Liu et al., 1995). The protein phosphorylation substrates, human $E_1\alpha$ and $E_1\beta$ PDC subunits, co-expressed and purified from *E. coli* M15, were obtained from Dr. Mulchand S. Patel of the Department of Biochemistry, School of Medicine and Biomedical Sciences, State University of New York at Buffalo, Buffalo, N.Y. This co-expressed $E_1\alpha$ and $E_1\beta$ system has been used extensively in the study of the regulation of PDC $E_1$ phosphorylation in mammalian systems (Korotchkina and Patel, 1995). For phosphorylation experiments, 20–25 µg of $E_1\alpha/\beta$ was combined with about 10 µg of YA5-accumulating *E. coli* cytosol protein, in a final volume of 100 µl containing 20 mM potassium phosphate, pH 7.0, 1 mM magnesium chloride, 2 mM dithiothreitol, 0. mM EDTA and 200 µM cold ATP. The mixture was pre-incubated at room temperature for 5 minutes, and then 5 µCi $^{32}$P-γ-ATP was added to start the assay. At 2, 5, 10, 15, and 20 minutes after starting the assay, 20 µl aliquots of the raction mixture were withdrawn and the reaction was stopped with 20 µl of SDS-denaturating mixture. Samples were then separated on 10% SDS-PAGE and autoradiographed to reveal $^{32}$P-labeled proteins.

Construction of YA5 Antisense Plant Transformation Vector for Constitutive Expression:

The YA5 cDNA contains internal BamHI (nt 628) and NcoI (nt1176) restriction sites. The BamHI and NcoI fragment was freed from YA5F and cloned into the respective sites in pBI524 (Datla et al., 1993), in an antisense orientation, under the control of a tandem 35S promoter. The YA5 antisense cassette was then excised from pBI524 by HindIII and EcoRI, and cloned into plant transformation vector pRD400 (Datla et al., 1992).

Construction of YA5 Antisense and Partial Sense Plant Transformation Vectors for Seed-Specific Expression The YA5 full-length cDNA (YA5F; 1.5 kb) was cloned in pBluescript SK (+/−) plasmid (Stratagene) in a 5' to 3' orientation of T7-T3. An 875 bp fragment was excised by a BamHI (Pharmacia) digestion and ligated into the plasmid pDH1 which had previosly been cut with BamHI and dephosphorylated (treated with ¹/₁₀ unit of calf intestine alkaline phosphatase for 1 hour at 37° C.). Plasmid pDH1 (provided by Dr. P. Covello, PBI/NRC) is the plasmid PE35SNT which has been manipulated so that the constitutive tandem 35S promoter has been excised and replaced with the seed-specific napin promoter, obtained from plasmid pUC19. Ligations were performed at 4–12° C. overnight in a waterbath, following the instructions provided by the manufacturer. Competent *E. coli* cells (DH5α, Gibco BRL) were transformed by a heat shock method, with 50–100 ng of transforming DNA, plated on a selective medium (LB with 50 µg/mL ampicillin) and incubated overnight at 37° C. The Bluescript plasmid DNA (10 ng) was used as a positive control for the transformation. Single transformed cells were grown overnight (37° C., 225 r.p.m.) in 5 mL LB with 50 µg/mL ampicillin. DNA extraction and purification was performed with a Qiaprep Spin Miniprep kit (Qiagen). Restriction digestions were performed with HindIII to check for the presence and the orientation of inserts in the plasmid. In the case of a YA5 insert in an anti-sense orientation, two fragments of about 1.0 and 1.4 Kb were obtained, while a YA5 insert in a sense orientation gave two fragments of about 1.8 and 0.6 Kb. The cassette and the insert (in either sense or anti-sense orientation) were excised by a partial double digestion with HindIII and EcoRI (1 unit/20 µL reaction for 10 min at 37° C.). The DNA fragments corresponding to the cassette with either the sense or anti-sense insert, were purified from the agarose gel using a Geneclean II Kit (Bio 101, Inc.) and ligated to the HindIII/EcoRI digested pRD400 plasmid. The best ligation results were obtained with a 1:10 plasmid to insert ratio in a 10 µL reaction volume, using 1 µL of T4 ligase and buffer (New England Biolabs) at 4° C. overnight. The reaction mixture was heated at 45° C. for 5 min and ice chilled prior to adding the ligase. The following day, 1 µL of T4 ligase was added and the mixture left at room temperature for a further 3–4 hrs. The identity of each construct was re-checked by digestion and DNA sequencing before plant transformation.

Transformation of *Arabidopsis thaliana*:

The transformation protocol was adapted from that described by Bechtold et al., (1993). Plants of *Arabidopsis thaliana* ecotype Columbia were grown in moist soil at a density of 10–12 plants per pot, in 4-inch square pots, and covered with a nylon screen fixed in place with an elastic band. Once the plants reached the stage at which bolts were just emerging, plants were watered, the bolts and some of the leaves were clipped, and the plants infiltrated in *Agrobacterium* suspension as outlined below.

To grow the *Agrobacterium*, a 25 mL suspension in LB medium containing kanamycin at a concentration of 50 µg/mL was cultured for two to three days ahead of time. The day before infiltration, this "seed culture" was added to 400 mL of LB medium containing 50 µg/mL kanamycin. Once the absorbance at 600 nm was >2.0, the cells were harvested by centrifugation (5,000×g, 10 min in a GSA rotor at room temperature) and resuspended in 3 volumes of infiltration medium (½×Murashige and Skoog salts, 1×B5 vitamins, 5.0% sucrose, 0.044 µM benzylaminopurine) to an optical density at 600 nm of 0.8. The *Agrobacterium* suspension was then poured into a beaker and the potted plants inverted into the beaker so that the bolts and entire rosettes were submerged. The beaker was then placed into a large Bell jar and a vacuum drawn using a vacuum pump, until bubbles formed on the leaf and stem surfaces and the solution started to bubble a bit, and then the vacuum was released rapidly. [Note: The necessary time and pressure will vary from one lab setup to the next, but good infiltration is visibly apparent as uniformly darkened, water-soaked tissue.] Pots were removed from the beaker, laid on their side in a plastic tray and covered with a plastic dome, to maintain humidity. The following day, the plants were uncovered, set upright and allowed to grow for approximately four weeks in a growth chamber under continuous light conditions as described by Katavic et al., (1995). When the siliques were mature and dry, seeds were harvested and selected for positive transformants.

Selection of Putative Transformants (Transgenic plants) and Growth and Analysis of Transgenic Plants:

Seeds harvested from vacuum-infiltratration transformation experiments were sterilized by treating for 1 min in ethanol and then 5 min in 50% bleach/0.05% Tween 20™ in sterile distilled water. Then the seeds were rinsed several times with sterile distilled water. Seeds were plated by resuspending them in sterile 0.1% agarose at room temperature (about 1 mL agarose for every 500–1000 seeds), and then applying a volume equivalent to about 2,000–4,000 seeds onto 150×15 mm selection plates (½×Murashige and Skoog salts, 0.8% agar, autoclave, cool and add 1×B5 vitamins and kanamycin at a final concentration of 50 μg/mL). The plates were dried in a laminar flow hood until seed no longer flowed when the plates were tipped. The plates were then vernalized for two nights at 4° C. in the dark, and then moved to a growth chamber (conditions as described by Katavic et al., 1995). After 7-10 days, transformants were clearly identifiable as dark green plants with healthy green secondary leaves and roots that extended over and into the selective medium.

Seedlings were transplanted to soil, plants grown to maturity and mature seeds ($T_2$ generation as defined in Katavic et al., 1994) collected and analyzed. $T_2$ seeds were propagated. The vegetative growth patterns were monitored by measuring shoot tissue dry weights, and/or by counting the number of rosette leaves present by the time plants began to enter the generative (flower initiation) stage. Floral initiation (beginning of generative phase of growth) was analyzed by recording, on a daily basis, the percentage of plants in which a flower bud first appeared and/or the percentage of plants that were bolting (as described by Zhang et al. 1997). Data was reported in terms of percentage of plants flowering/bolting on a given day after planting (d.a.p.).

Preparation of Mitochondria from *A. thaliana* Non-Transformed Control and Anti-YA5 Transgenic Plants All extractions were performed at 4° C. An enriched mitochondrial fraction was prepared by a procedure modified from Ap Rees et al., (1993). About 30 g of freshly-harvested shoots were homogenized using a chilled Waring Bleder in 4 volumes of extraction buffer (50 mM Tris-HCl, pH 8.0, containing 300 mM mannitol, 5 mM EDTA, 0.1% bovine serum albumin, 1% PVPP (polyvinylpolyppyrrolidone) and 9 mM 2-mercaptoethanol. The homogenate was filtered through four layers of cheesecloth and one layer of Miracloth and centrifuged at 2,000×g for 10 min. The pellet was discarded and the supernatant centrifuged at 10,000×g for 30 min. The pellet was resuspended in the extraction buffer minus PVPP and used as an "enriched" mitochondrial preparation. For the succinate dehydrogenase activity measurements, this preparation was used directly. For measurements of PDC, fumarase and citrate synthase, the freshly-prepared mitochondria were first lysed in the presence of 0.1% (v/v) Triton X-100 to release the mitochondrial enzymes. The Triton lysate was clarified by centrifugation at 27,000×g and the supernatant, containing solubilized enzymes, was concentrated with a Centricon-30 filter concentrator (Amicon). The resulting concentrate was used as the enzyme source in a PDC assay. Protein concentrations were estimated by the method of Bradford (1976) using bovine serum albumin as a standard, and normalized prior to assay.

Pyruvate Dehydrogenase Complex Assay:

The method used to determine the pyruvate dehydrogenase (PDH) complex activity present in mitochondrial protein preparations was modified from the method of Reid et al., (1977). The assay mixture consisted of 0.1 mM TPP, 5 mM $MgCl_2$, 1.5 mM $NAD^+$, 0.1 mM Coenzyme A, 3.0 mM cysteine-HC and 1.5 mM pyruvate in 100 mM Tricine pH 8.0, in a final volume of 2 mL. Reactions were initiated by the addition of mitochondrial lysate concentrate. Control reactions contained all components except pyruvate. The reaction mixture was incubated at 30° C. and the formation of NADH was monitored at a wavelength of 340 nm at 15-second intervals for 3 minutes, using a Beckman DU 74 spectrophotometer.

Citrate Synthase Assay:

The method used to measure citrate synthase activity present in mitochondrial protein preparations was modified from the method of Srere (1969). The reaction mixture contained 0.2 mM 5', 5'-dithiobis-2-nitrobenzoic acid (DTNB), 0.1 mM acetyl-CoA, and mitochondrial lysate protein, in 50 mM Tris-HCl, pH 7.8, in a final reaction volume of 2 mL, incubated at 30° C. The absorption at 412 nm was followed for 3 minutes to measure possible acetyl-CoA deacylase activity. The citrate synthase reaction was then started by the addition of 0.5 mM oxaloacetate (OAA), and the release of Coenzyme A (CoASH), the SH group of which reacts with the DTNB (Ellman's reagent), was monitored at 412 nm. The resulting mercaptide ion has a strong absorption (E=13,600) at 412 nm. Control reactions contained all components except OAA.

Fumarase Assay:

Fumarase activity present in mitochondrial protein preparations was assayed by the method of Hill and Bradshaw (1969). The reaction mixture contained 25 mM sodium malate and mitochondrial lysate protein in 50 mM sodium phosphate buffer, pH 7.5, in a final reaction volume of 1 mL. Reactions were incubated at 28° C. Fumarase activity, measured by the formation of fumarate, was determined spectrophotometrically by monitoring the increase in absorbance at 250 nm, at 15-second intervals for two minutes.

Succinate Dehydrogenase Assay:

Mitochondrial succinate dehydrogenase activity was measured using the method of Veeger et al., (1969). The reaction mixture contained 1 mM KCN. 40 mM succinate, 1 mM EDTA, 0.1% BSA, 3 mM $K_3Fe(CN)_6$, 0.1% Triton X-100 and unlysed mitochondria in 100 mM sodium phosphate buffer at pH 7.5, in a final reaction volume of 1 mL. Reaction mixtures were incubated at 28° C. The reaction was initiated by the addition of mitochondria in oxygen-free phosphate buffer. The change in absorbance at 455 nm was monitored spectrophotometrically, at 20-second intervals for 2 minutes. Control reactions contained all components except succinate.

Seed Lipid Analyses of Seeds from *A. thaliana* Non-Transformed Controls and Anti-Sense PDHK (AsYA5) Transgenics:

Mature siliques and $T_2$ or $T_3$ seeds were isolated from anti-sense PDHK transformants (designated as YA5 lines) or pBI121 control transformants (without anti-sense PDHK, but with a kanamycin resistance gene) and siliques and seeds were also isolated from non-transformed wild-type control plants and their respective seed oil contents, fatty acyl compositions of the seed oils, average seed weights, number of siliques per 15 cm segment of bolting stem and number of seeds per silique were determined as described by Zou et al., (1997). All plants were grown in the same growth chamber, at the same time and under identical light and temperature regimes, as described previously (Katavic et al., 1995; Zou et al., 1997). Because of the extremely small seed size and weight, analyses were performed on 100- or 400-seed replicates that were carefully counted out under a dissecting microscope. Seed samples were ground using a polytron in chloroform:isopropanol (2:1, [v/v]) containing 0.2% w/v butylated hydroxytoluene and tripentadecanoin as an internal standard. All other conditions for the isolation and analysis of seed total fatty acid content and fatty acid composition (expressed as wt % of total fatty acids) by gas chromatography were performed as detailed previously (Taylor et al., 1992b; Taylor et al., 1995; Katavic et al., 1995, Zou et al., 1997). Oil content was expressed either as μg of total fatty acids per sample size (See, FIG. 10), or as mg of oil per sample size (See, Table 1), calculated by assuming 3 moles of fatty acids per mole of triacylglycerol (oil), as described by Zou et al., (1997).

What is claimed is:

1. A method of modulating the level of PDK protein in a plant, comprising:
   a) stably transforming a plant cell with a plant PDK polynucleotide operably linked to a promoter, wherein the polynucleotide is in sense or antisense orientation;
   b) growing the plant cell under plant growing conditions to produce a regenerated plant; capable of expressing the polynucleotide for a time sufficient to modulate the PDK protein in the plant.

2. The method of claim 1, wherein PDK protein is increased.

3. The method according to claim 1, characterized in that said plant is a member of the group consisting of Canola, corn (*Zea mays*), cotton (*Gossypium* spp), sunflower (*Helianthus* spp.), wheat (*Triticum* spp.), barley (*Hordeum* spp.), rice (*Oryza* spp.), and sorghum (*Sorghum* spp.).

4. The method of claim 1, wherein PDK protein is decreased.

5. A method for controlling carbon flow into the Krebs cycle in plants comprising modulating PDK protein expression by the method of claim 1.

6. A method for increasing oil content in a plant by modulating PDK protein expression by the method of claim 1.

* * * * *

UNITED STATES PATENT AND TRADEMARK OFFICE
CERTIFICATE OF CORRECTION

PATENT NO. : 6,825,039 B2  Page 1 of 1
APPLICATION NO. : 10/202428
DATED : November 30, 2004
INVENTOR(S) : Jitao Zou and David C. Taylor It is certified that error appears in the above-identified patent and that said Letters Patent is hereby corrected as shown below:

In the specification:
COLUMN 14, LINE 51, change "1014 65%" to --10-65%--
COLUMN 17, LINE 1, change "of*A*." to --of *A*.--

Signed and Sealed this

Fourteenth Day of July, 2009

JOHN DOLL
*Acting Director of the United States Patent and Trademark Office*